US010086010B2

(12) United States Patent
Matsumoto et al.

(10) Patent No.: US 10,086,010 B2
(45) Date of Patent: Oct. 2, 2018

(54) SYNERGISTIC ENHANCEMENT OF 5-FLUOROURACIL CYTOTOXICITY BY DEOXYURIDINE ANALOGS IN CANCER CELLS

(71) Applicants: STC.UNM, Albuquerque, NM (US); Hiroshi Ide, Higashi-Hiroshima (JP)

(72) Inventors: Yoshihiro Matsumoto, Kasugai (JP); Alan Edward Tomkinson, Albuquerque, NM (US); Hiroshi Ide, Higashi-Hiroshima (JP)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 15/126,777

(22) PCT Filed: Mar. 17, 2015

(86) PCT No.: PCT/US2015/020991
§ 371 (c)(1),
(2) Date: Sep. 16, 2016

(87) PCT Pub. No.: WO2015/142867
PCT Pub. Date: Sep. 24, 2015

(65) Prior Publication Data
US 2018/0125875 A1   May 10, 2018

Related U.S. Application Data

(60) Provisional application No. 61/954,747, filed on Mar. 18, 2014.

(51) Int. Cl.
| | |
|---|---|
| *A01N 43/04* | (2006.01) |
| *A61K 31/70* | (2006.01) |
| *A61K 31/7072* | (2006.01) |
| *A61K 31/513* | (2006.01) |
| *A61P 35/00* | (2006.01) |
| *A61K 45/06* | (2006.01) |
| A61K 31/7064 | (2006.01) |
| A61K 31/706 | (2006.01) |
| A61K 31/7068 | (2006.01) |

(52) U.S. Cl.
CPC ........ *A61K 31/7072* (2013.01); *A61K 31/513* (2013.01); *A61K 45/06* (2013.01); *A61P 35/00* (2018.01); A61K 31/706 (2013.01); A61K 31/7064 (2013.01); A61K 31/7068 (2013.01); A61K 2300/00 (2013.01)

(58) Field of Classification Search
None
See application file for complete search history.

(56) References Cited

U.S. PATENT DOCUMENTS

| | | |
|---|---|---|
| 7,648,967 B2 | 1/2010 | Li et al. |
| 8,445,537 B2 | 5/2013 | Tomkinson et al. |
| 8,617,540 B2 | 12/2013 | Matsumoto |
| 2005/0148534 A1 | 7/2005 | Castellino et al. |
| 2010/0266565 A1 | 10/2010 | Matsumoto |
| 2012/0219522 A1 | 8/2012 | Xi |

FOREIGN PATENT DOCUMENTS

| | | |
|---|---|---|
| WO | 9420069 A1 | 9/1994 |
| WO | 2008083465 A1 | 7/2008 |
| WO | 2011153382 A1 | 12/2011 |

OTHER PUBLICATIONS

Grem JL. 5-Fluorouracil: forty-plus and still ticking. A review of its preclinical and clinical development. Investigational New Drugs 2000;18:299-313.
O'Connor OA. Pharmacological Modulation of Fluoropyrimidines: Building on the Lessons of the Past. In: Schwartz GK, editor. Combination Cancer Therapy: Modulators and Potentiators. Totowa, NJ: Humana Press; 2005 p. 133-174.
Yoshida K, et al. Challenge for a better combination with basic evidence. Int J Clin Oncol 2008; 13:212-9.
Lewis HL, et al. Serologic assay of DNA base damage. I. 5-Hydroxymethyldeoxyuridine, a radiation product of thymidine. Radiation Research 1978;75:305-16.
Teebor GW, et al. Ionizing radiation and tritium transmutation both cause formation of 5-hydroxymethyl-2'-deoxyuridine in cellular DNA. Proc Natl Acad Sci USA 1984;81:318-21.
Kahilainen LI, et al. 5-Hydroxymethyl-2'-deoxyuridine. Cytotoxicity and DNA incorporation studied by using a novel [2-14C]-derivative with normal and leukemic human hematopoietic cells. Acta Chemi Scand 1985;39:477-84.
Meldrum JB, et al. Toxicologic and antitumor studies on 5-hydroxymethyldeoxyuridine. Toxicol Appl Pharmacol 1985;79:423-35.
Kahilainen L, et al. In vitro and in vivo studies of a promising antileukemic thymidine analogue, 5-hydroxymethyl-21 deoxyuridine. Biochem Pharmacol 1986;35:4211-5.
Vilpo JA, et al. Antileukemic activity against L1210 leukemia, pharmacokinetics and hematological side effects of 5-hydroxymethyl-2'-deoxyuridine. Leuk Res 1987;11:877-80.

(Continued)

Primary Examiner — Patrick T Lewis
(74) *Attorney, Agent, or Firm* — Henry D. Coleman; R. Neil Sudol

(57) ABSTRACT

In one embodiment, the invention provides a method of treating a subject who suffers from a neoplasm (including a cancer such as a radiotherapeutic-resistant cancer) by administering to the subject a therapeutically effective amount of (a) 5-formyl-2'-deoxyuridine (fdU or foUdR) or a 5-formyl-2'-deoxyuridine derivative, optionally in combination with 5-hydroxy-2'-deoxyuridine (hUdR); and (b) at least one composition selected from the group consisting of either 5-fluorouracil (5-FU), a 5-FU prodrug (e.g. 5-fluoro-2'-deoxyuridine (FdU)) or 5-FU metabolite. In a preferred embodiment, a subject who suffers from colorectal cancer (CRC) or metastatic colorectal cancer (mCRC) is treated with a therapeutically-effective amount of fdU and either 5-FU or the 5-FU prodrug 5-fluoro-2'-deoxyuridine (FdU). Related pharmaceutical compositions are also provided.

41 Claims, 13 Drawing Sheets

(56) References Cited

OTHER PUBLICATIONS

Vilpo JA, Vilpo LM. Metabolism, incorporation into DNA, and interactions with I-beta-D-arabino5-FUranosylcytosine of 5-hydroxymethyl-2'-deoxyuridine in human promyelocytic leukemia cells (HL-60). Cancer Res 1988;48:3117-22.
Yoshida M, et al. Substrate and mispairing properties of 5-formyl-2'-deoxyuridine 6-triphosphate assessed by in vitro DNA polymerase reactions. Nucleic Acids Res 1997;25:1570-7.
Zong WX, et al. Alkylating DNA damage stimulates a regulated form of necrotic cell death. Genes Dev 2004;18:1272-82.
Reynolds CP, Maurer BJ. Reynolds CP, Maurer BJ. Evaluating response to antineoplastic drug combinations in tissue culture models. Methods Mol Med 2005;110:173-83.
Rogstad DK, et al. Measurement of the incorporation and repair of exogenous 5-hydroxymethyl-2'-deoxyuridine in human cells in culture using gas chromatography-negative chemical ionization-mass spectrometry. Chem Res Toxicol 2007;20:1787-96.
Schreiber V, et al. Poly(ADP-ribose): novel 5-FUnctions for an old molecule. Nat Rev Mol Cell Biol 2006;7:517-28.
Vaculova A, et al. Different modulation of TRAIL-induced apoptosis by inhibition of pro-survival pathways in TRAIL-sensitive and TRAIL-resistant colon cancer cells. FEBS Lett 2006;580:6565-9.
Caserta TM, et al. Q-VD-OPh, a broad spectrum caspase inhibitor with potent antiapoptotic properties. Apoptosis 2003;8:345-52.
Bjorkoy G, et al. p62/SQSTM1 forms protein aggregates degraded by autophagy and has a protective effect on huntingtin-induced cell death. J. Cell Biol 2005;171 :603-14.
Kabeya Y, et al. LC3, a mammalian homologue of yeast Apg8p, is localized in autophagosome membranes after processing. EMBO J 2000; 19:5720-8.
Degterev A, et al. Chemical inhibitor of nonapoptotic cell death with therapeutic potential for ischemic brain injury. Nat Chem Biol 2005;1:112-9.
Edinger AL, Thompson CB. Death by design: apoptosis, necrosis and autophagy. Curr Opin Cell Biol 2004; 16:663-9.
Chou TC, Talalay P. Quantitative analysis of dose-effect relationships: the combined effects of multiple drugs or enzyme inhibitors. Adv Enzyme Regul 1984;22:27-55.
Papadopoulos N, et al. Mutation of a mutL homolog in hereditary colon cancer. Science 1994;263: 1625-9.
Berger SH, et al. A naturally occurring variation in thymidylate synthase structure is associated with a reduced response to 5-fluoro-2'-deoxyuridine in a human colon tumor cell line. Mol Pharmacol 1988;34:480-4.
Berger SH, Berger FG. Thymidylate synthase as a determinant of 5-fluoro-2'-deoxyuridine response in human colonic tumor cell lines. Mol Pharmacol 1988;34:474-9.
Pettersen HS, et al. UNG-initiated base excision repair is the major repair route for 5-fluorouracil in DNA, but 5-fluorouracil cytotoxicity depends mainly on RNA incorporation. Nucleic Acids Res 2011;39:8430-44.
Peralta-Leal A, et al. Poly(ADP-ribose)polymerase-1 (PARP-1) in carcinogenesis: potential role of P ARP inhibitors in cancer treatment. Clin Transl Oncol 2008;10:318-23.
Boorstein RJ, et al. Definitive identification of mammalian 5-hydroxymethyluracil DNA N-glycosylase activity as SMUGI. J Biol Chem 2001;276:41991-7.
An Q, et al. 5-Fluorouracil incorporated into DNA is excised by the Smugl DNA glycosylase to reduce drug cytotoxicity. Cancer Res 2007 ;67 :940-5.
Kunz C, et al. Base excision by thymine DNA glycosylase mediates DNA-directed cytotoxicity of 5-fluorouracil. PLoS Biol 2009;10. 1371/journal.pbio.1000091.
Boorstein RJ, et al. A mammalian cell line deficient in activity of the DNA repair enzyme 5-hydroxymethyluracil-DNA glycosylase is resistant to the toxic effects of the thymidine analog 5-hydroxymethyl-2'-deoxyuridine. Mol Cell Biol 1992;12:5536-40.
Masaoka A, et al. Mammalian 5-formyluracil-DNA glycosylase. 2. Role of SMUG 1 uracil-DNA glycosylase in repair of 5-formyluracil and other oxidized and dearninated base lesions. Biochemistry 2003;42:5003-12.
Nemec AA, et al. Colon cancer-associated DNA polymerase 13 variant induces genomic instability and cellular transformation. J Biol Chem 2012;287:23840:-9.
Einolf HJ, Guengerich FP. Kinetic analysis of nucleotide incorporation by mammalian DNA polymerase delta. J Biol Chem 2000; 275:16316-22.
Langen P.et al.; 5-Formyl-2'-deoxyuridiine: cytostatic and antiviral properties and possible modes of action. Acta Biol Med Ger, 1976; 35(12): 1625-1633 (Abstract).

SYNERGISTIC ENHANCEMENT OF 5-FLUOROURACIL CYTOTOXICITY BY DEOXYURIDINE ANALOGS IN CANCER CELLS

CROSS REFERENCE TO RELATED APPLICATIONS

This application is a United States national phase patent application based upon International patent application number PCT/US2015/020991 of International filing date Mar. 17, 2015 which claims priority from U.S. Provisional Patent Application No. U.S. 61/954,747, entitled "Combination Treatment with 5-Fluorouracil and 5-Formyl-2'-Deoxyuridine for Cancer Therapy", filed Mar. 18, 2014. The complete contents of these two documents are hereby incorporated herein in their entirety.

STATEMENT REGARDING FEDERAL 5-FUNDING

This invention was made without government funding.

FIELD OF THE INVENTION

In one embodiment, the invention provides a method of treating a subject who suffers from a neoplasm (including a cancer such as a radiotherapeutic-resistant cancer) by administering to the subject a therapeutically effective amount of (a) 5-formyl-2'-deoxyuridine (fdU or foUdR) or a 5-formyl-2'-deoxyuridine derivative, optionally in combination with 5-hydroxy-2'-deoxyuridine (hUdR); and (b) at least one composition selected from the group consisting of either 5-fluorouracil (5-FU), a 5-FU prodrug (e.g. 5-fluoro-2'-deoxyuridine (FdU)) or a 5-FU metabolite. In a preferred embodiment, a subject who suffers from colorectal cancer (CRC) or metastatic colorectal cancer (mCRC) is treated with a therapeutically-effective amount of fdU and either 5-FU or the 5-FU prodrug 5-fluoro-2'-deoxyuridine (FdU). Related pharmaceutical compositions are also provided.

BACKGROUND OF THE INVENTION

Since its first rational development in 1957, 5-fluorouracil (5-FU) has been widely used as a chemotherapy reagent for various types of cancers, including colorectal, breast and pancreatic cancers (1). 5-FU is an antimetabolite that exerts its cytotoxic effect via several different mechanisms. These include reducing dTTP levels by inhibition of thymidylate synthase, misincorporation of both dUTP and FdUTP during DNA replication and repair of misincorporated dUTP and FdUTP, misincorporation of 5-FUTP into RNA and disruption of several aspects of RNA metabolism. Through its long history, the mechanism of action of 5-FU has been studied extensively, and a number of derivatives and combination therapies with other types of therapeutics have been developed to improve its effectiveness (2). Nevertheless these combination therapies often increase the risk of severe side effects limiting clinical application, and many tumor types exhibit a low response rate and/or rapidly acquire resistance (3).

5-Hydroxymethyl-2'-deoxyuridine (hmUdR) is a deoxyuridine analog, which can be formed by oxidation of thymine in cellular DNA exposed to ionizing radiation (4, 5). When added to culture medium, hmUdR is incorporated into cellular DNA, causing cytotoxicity in tumor cells (6-9). Interestingly, it has been reported that hmUdR synergistically enhances the growth inhibitory activity of 1-β-D-arabino5-FUranosylcytosine (Ara-C) by increasing the incorporation of the modified nucleoside into cellular DNA (10).

While examining the cytotoxicity of a number of base adducts generated by ionizing radiation, we found that a combination of 5-FU and hmUdR inhibited cell proliferation much more potently than either compound alone. We have demonstrated that hmUdR and other deoxyuridine analogs synergistically enhance the cytotoxicity of 5-FU in cancer but not normal cells by dramatically increasing the number of single strand breaks. See U.S. Pat. No. 8,617,540.

Extending our therapeutic and mechanistic understandings regarding cancer treatments using 5-FU and hmUdR to develop other synergistic 5-FU-based co-therapies would prove to be of great benefit to patients who suffer from cancers such as colorectal cancer (CRC).

SUMMARY OF THE INVENTION

Here we demonstrate that 5-formyl-2'-deoxyuridine (fdU or foUdR) (optionally combined with 5-hydroxy-2'-deoxyuridine (hUdR)) synergistically enhances the cytotoxicity of 5-FU, 5-FU prodrugs and 5-FU metabolites in cancer cells, but not normal cells, by dramatically increasing the number of single strand breaks. For example, as explained in greater detail hereinafter, we have discovered that: (1) a combination treatment of a colon cancer cell line, HT-29, with fdU and either 5-FU or the 5-FU prodrug FdU caused cell growth inhibition in a synergistic manner (FIG. 2A) (2) a clonogenic assay of this treatment suggests that the treatment with fdU and 5-FU causes cell death rather than growth inhibition (FIG. 3A), and (3) this treatment leads to accumulation of S-phase cells (FIG. 4A).

Thus, in one embodiment, the invention provides a method of treating a subject who suffers from a neoplasm (including a cancer), the method comprising administering to the subject a therapeutically effective amount of:

(a) 5-formyl-2'-deoxyuridine (fdU) or a 5-formyl-2'-deoxyuridine (fdU) derivative, optionally in combination with 5-hydroxy-2'-deoxyuridine (hUdR); and (b) at least one composition selected from the group consisting of (1) 5-fluorouracil (5-FU) (2) a 5-FU prodrug (including but not limited to 5-fluoro-2'-deoxyuridine (FdU), 5'-deoxy-5-fluoro-N-[(pentyloxy) carbonyl]-cytidine (Capecitabine), 13F-1 (a 5-fluorouracil prodrug containing an Asn-Gly-Arg ($NO_2$) $COOCH_3$ tripeptide), 1-(2-tetrahydro5-FUryl)-5-fluorouracil, 3,5-dioctanoyl 5-fluoro-2-deoxyuridine, UFT (ftora5-FUr (FTO) and uracil), 5-1 (ftora5-FUr (FTO) and 5-chloro-2,4-dihydroxypyridine plus potassium oxonate), 5-FA-PAE (5-fluorouracil-1 acetic acid (5-FA) coupled with PEG derivatives by an ester bond), 5-FU-lipid conjugates, hyaluronan-5-fluorouracil conjugate (HA-5-5-FU), cholesteryl-hexahydrophthaloyl-5-fluorouracil (CHHP-5-5-FU) and tega5-FUr (tetrahydro5-FUranyl-5-fluorouracil) and uracil (1:4), and (3) a 5-FU metabolite (e.g. fluorodeoxyuridine monophosphate (FdUMP), fluorodeoxyuridine triphophate (FdUTP) or fluorouridine triphophate (FUTP)).

Therapeutically useful "5-formyl-2'-deoxyuridine (fdU) derivatives" include, but are not limited to, oxime and dithiolane derivatives of 5-formyl-2'-deoxyuridine, oligodeoxynucleotides which incorporate 5-formyl-2'-deoxyuridine, enamine derivatives of 5-formyl-2'-deoxyuridine and 5-formyl-2'-deoxyuridine-5'-triphosphate.

In methods of treatment and pharmaceutical compositions of the invention, 5-formyl-2'-deoxyuridine (fdU) or its derivatives may be in the form of a mixture of α-anomers and β-anomers, or may be administered in the form of a substantially purified α-anomer or a substantially purified β-anomer. The sugar group of 5-formyl-2'-deoxyuridine (fdU), fdU derivative and/or 5-hydroxy-2'-deoxyuridine may be halogenated (e.g. with either chlorine or fluorine).

In certain embodiments, 5-formyl-2'-deoxyuridine (fdU) is protected by converting the 5-formyl-2'-deoxyuridine (fdU) carbonyl group to either an acetal or hydrazide group ex vivo; the acetal and hydrazine group convert in vivo to a carbonyl group.

In preferred embodiments (1) 5-formyl-2'-deoxyuridine (fdU) or fdU derivative and optional 5-hydroxy-2'-deoxyuridine (hUdR) and (2) 5-fluorouracil (5-FU) and/or 5-fluoro-2'-deoxyuridine (FdU) are administered concomitantly to a subject suffering from a cancer (e.g. colorectal cancer (CRC) or metastatic colorectal cancer (mCRC).

In certain embodiments, depending upon clinical assessments and treatment goals, the subject is also treated concomitantly by additional therapies or therapeutic agents selected from the group consisting of one or more additional chemotherapeutic agents such as paclitaxel and docetaxel, platinum-based antineoplastics (e.g. cisplatin, carboplatin, oxaliplatin, satraplatin, picoplatin, Nedaplatin, Triplatin, and Lipoplatin), hormonal therapy, proton therapy, cryosurgery, and/or high intensity focused ultrasound (HIFU).

As described in further detail hereinafter, we have also discovered that 5-formyl-2'-deoxyuridine (fdU or foUdR) synergistically enhances the cytotoxicity of 5-FU in cancer cells at dosages that are lower than the 5-hydroxymethyl-2'-deoxyuridine (hmUdR) dosages used in our 5-FU-hmUdR anti-cancer co-therapies. This ability to lower therapeutic dosages will enhance patient compliance, increase the likelihood of a favorable clinical outcome and reduce the cost of treatments. Consequently, the methods and formulations described herein prove particularly effective in treating a wide variety of cancers that have been previously been associated with high rates of remission and poor long-term survival.

These and other aspects of the invention are described further in the Detailed Description of the Invention.

DETAILED DESCRIPTION OF THE INVENTION

Figure 1:
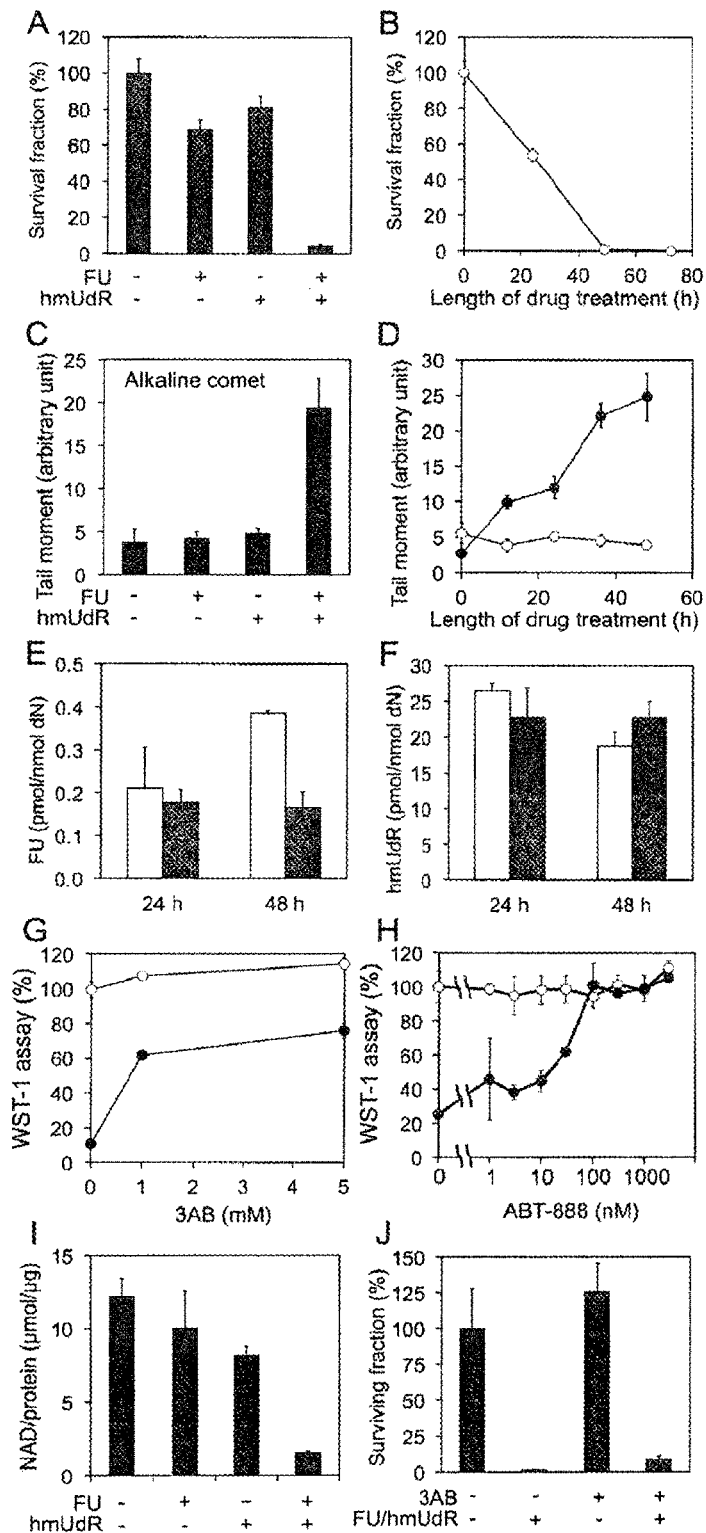
FIG. 1. Properties of the synergistic toxicity by 5-FU and hmUdR. (A) Colony formation assays of HT-29 cells treated for 48 h with or without 0.5 µM 5-FU and/or 5 µM hmUdR. (B) Time course of effects of 5-FU and hmUdR in colony formation assay. (C) Alkaline comet assays for detection of single-strand breaks (SSBs) in HT-29 cells treated for 48 h with indicated combinations of 0.5 µM 5-FU and 5 µM hmUdR. (D) Time course of SSB formation. The SSB formation was quantitated in HT-29 cells treated with (●) or without (○) 0.5 µM 5-FU and 5 µM hmUdR. (E) Incorporation of 5-FU into HT-29 cellular DNA. Incorporation of tritium-labeled 5-FU (0.5 µM in the medium) was measured in the absence (□) or the presence (■) of 5 µM hmUdR and presented as picomoles per nanomoles of deoxynucleosides. (F) Incorporation of hmUdR into HT-29 cellular DNA. Incorporation of tritium-labeled hmUdR (5 µM in the medium) was measured in the absence (□) or the presence (■) of 0.5 µM 5-FU and presented as picomoles per nanomoles of deoxynucleosides. All data except panel E are from triplicate experiments and plotted with standard deviations. Data in panel E are from duplicate experiments and plotted with deviations. (G) Effects of 3-aminobenzamide (3AB), a broad PARP inhibitor on the cytotoxicity by 5-FU and hmUdR. 3AB was titrated for its effect on the HT-29 cell growth in the absence (○) or the presence (●) of 0.5 µM 5-FU and 5 µM hmUdR. 3AB was added to the medium simultaneously with 5-FU and hmUdR. The cell growth was measured by WST-1 assay. (HC) Effects of ABT-888, a specific inhibitor for PARP1 and PARP2, on the cytotoxicity by 5-FU and hmUdR. ABT-888 was titrated for its effect on the HT-29 cell growth in the absence (○) or the presence (●) of 1 µM 5-FU and 10 µM hmUdR. ABT-888 was added to the medium simultaneously with 5-FU and hmUdR. The cell growth was measured by WST-1 assay. (I) Effect of 5-FU and hmUdR on cellular NAD levels. The quantities of NAD in cell extracts were normalized with the protein concentrations of the extracts. (J) Survival fractions of HT-29 cells treated with drugs in the presence of 3AB for 72 h. After replating without drugs, the cells were allowed to grow for 6 days and their nucleic acids were quantitated by CyQUANT kit. Data in panels B-E are from triplicate experiments and plotted with standard deviations.
Figure 2:
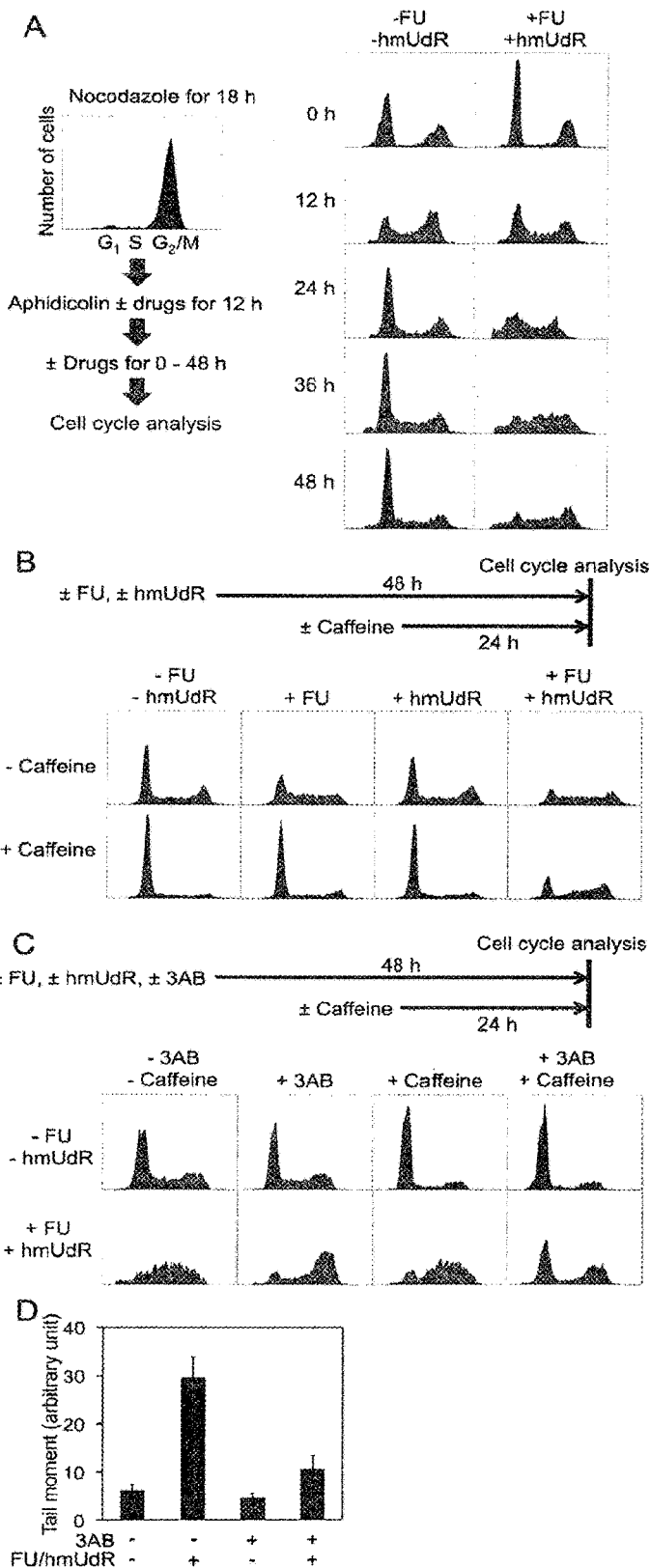
FIG. 2. Cell cycle analyses of HT-29 cells by flow cytometry. (A) Time course of cell cycle distribution of synchronized cells treated with a combination of 0.5 µM 5-FU and 5 µM hmUdR. HT-29 cells were synchronized at the $G_1/S$ boundary by sequential pretreatment with nocodazole and aphidicolin as described in Materials and Methods. The time at which aphidicolin was removed is designated 0 h. When indicated, 5-FU and hmUdR were added through aphidicolin treatment and subsequent incubation. (B) Effect of 5-FU, hmUdR and caffeine on cell cycle distribution. Unsynchronized HT-29 cells were treated without or with 0.5 µM 5-FU and 5 µM hmUdR for 48 h, and incubated in the absence or presence of 5 mM caffeine for the last 24 h. (C) Cell cycle analyses of unsynchronized HT-29 cells in the presence of 3AB and caffeine. (D) Alkaline comet assay of HT-29 cells treated for 48 h with drugs in the presence of 3AB. In both experiments, 0.5 µM 5-FU, 5 µM hmUdR and 3 mM 3AB were added when indicated. Data in panel B are from triplicate experiments and plotted with standard deviations.
Figure 3:
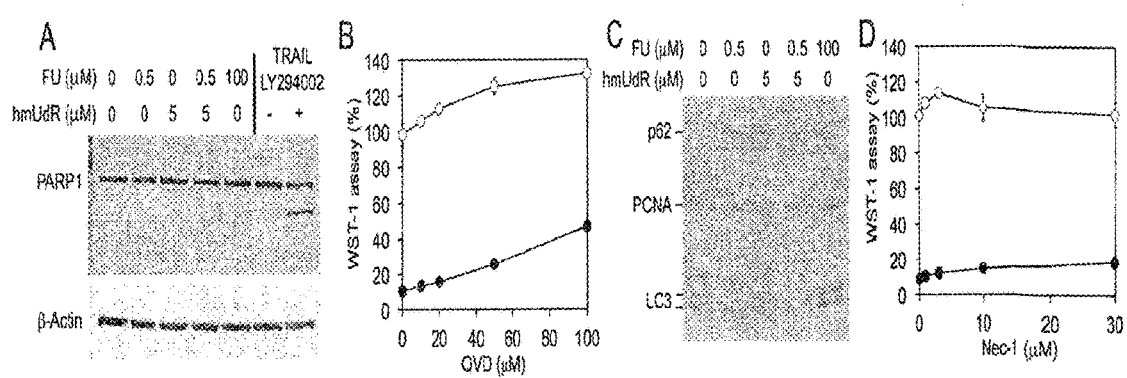
FIG. 3. Characterization of the mechanism for cell death resulting from combined treatment with 5-FU and hmUdR. (A) Immunoblot detection of PARP1. PARP1 cleavage was examined in whole cell extracts of HT-29 cells treated for 72 h with indicated concentrations of 5-FU and hmUdR. As a positive control for PARP1 cleavage, HT-29 cells were treated with 50 µM LY294002 for 1 h followed by 4 h treatment with 100 µg/ml TRAIL. β-Actin was a loading control. (B) Effects of an apoptosis inhibitor. A broad spectrum caspase inhibitor, QVD, were tested for their effects on the HT-29 cell growth in the absence (○) or the presence (●) of 0.5 µM 5-FU and 5 µM hmUdR. QVD was added to the medium simultaneously with 5-FU and hmUdR. The cell growth was measured by WST-1 assay. The slight increase in cell growth with 50 and 100 µM QVD was an effect of DMSO in which QVD was dissolved. (C) Immunoblot detection of autophagy-related proteins, p62 and LC3 (microtubule-associated protein 1 light chain 3). p62, LC3 and a loading control, PCNA, were detected in the whole cell extracts prepared by the same way as for panel A. Autophagy is expected to decrease p62 and increase the LC3 proteins. (D) Effects of a necroptosis inhibitor on the cytotoxicity by 5-FU and hmUdR. Necrostatin-1 (Nec-1) was tested for their effects on the HT-29 cell growth in the absence (○) or the presence (●) of 0.5 µM 5-FU and 5 µM hmUdR. Nec-1 was added to the medium simultaneously with 5-FU and hmUdR. The cell growth was measured by WST-1 assay. Data in panels B and D are from triplicate experiments and plotted with standard deviations.

The following terms are used throughout the specification to describe the present invention. Where a term is not given a specific definition herein, that term is to be given the same meaning as understood by those of ordinary skill in the art. The definitions given to the disease states or conditions which may be treated using one or more of the compounds according to the present invention are those which are generally known in the art.

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "patient" or "subject" is used throughout the specification to describe an animal, preferably a human, to whom treatment, including prophylactic treatment, with the compositions according to the present invention is provided (a patient or subject in need). For treatment of those infections, conditions or disease states which are specific for a specific animal such as a human patient, the term patient refers to that specific animal. In many instances, methods of treatment of the invention are administered to patients or subjects who are suspected of suffering from a cancer or who have been diagnosed as suffering from a cancer.

The term "compound" is used herein to refer to any specific chemical compound disclosed herein and in particular, arsenic trioxide. Within its use in context, the term generally refers to a small molecule, including a nucleoside or nucleoside analog as disclosed herein, but in certain instances may also refer to other forms of the compound. The term compound includes active metabolites of compounds and/or pharmaceutically acceptable salts thereof.

The terms "effective amount" and "therapeutically effective amount" are used throughout the specification to describe concentrations or amounts of formulations or other components which are used in amounts, within the context of their use, to produce an intended effect according to the present invention, in this case to treat a cancer or symptoms associated with a cancer, or to attempt to maintain a cancer in a state of remission.

The methods of treatment and formulations of the invention may be used to produce a favorable change in a cancer or cancer-related condition or symptom, whether that change is a remission of a cancer or related conditions or symptoms, a favorable physiological result, a reversal or attenuation of a cancer or related conditions or symptoms, the prevention or the reduction in the likelihood of a cancer or related conditions or symptoms occurring. Where formulations are used in combination, each of the formulations is used in an effective amount, wherein an effective amount may include a synergistic amount. The amount of formulation used in the present invention may vary according to the nature of the formulation, the age and weight of the patient and numerous other factors which may influence the bioavailability and pharmacokinetics of the formulation, the amount of formulation which is administered to a patient generally ranges from about 0.001 mg/kg to about 50 mg/kg or more, about 0.5 mg/kg to about 25 mg/kg, about 0.1 to about 15 mg/kg, about 1 mg to about 10 mg/kg per day and otherwise described herein. The person of ordinary skill may easily recognize variations in dosage schedules or amounts to be made during the course of therapy.

The term "prophylactic" is used to describe the use of a formulation described herein which reduces the likelihood of an occurrence of a condition or disease state in a patient or subject. The term "reducing the likelihood" refers to the fact that in a given population of patients, the present invention may be used to reduce the likelihood of an occurrence, recurrence or metastasis of disease in one or more patients within that population of all patients, rather than prevent, in all patients, the occurrence, recurrence or metastasis of a disease state.

The term "pharmaceutically acceptable" refers to a salt form or other derivative (such as an active metabolite or prodrug form) of the present compounds or a carrier, additive or excipient which is not unacceptably toxic to the subject to which it is administered.

"Treat", "treating", and "treatment", etc., as used herein, refer to any action providing a benefit to a patient at risk for or afflicted with a cancer, including improvement in the patient's condition through lessening or suppression of at least one symptom, delay in progression of the disease, prevention or delay in the onset of the disease, etc. Treatment, as used herein, encompasses both prophylactic and therapeutic treatment.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Cancers generally show partial or complete lack of structural organization and functional coordination with the normal tissue and most invade surrounding tissues, metastasize to several sites, and are likely to recur after attempted removal and to cause the death of the patient unless adequately treated. As used herein, the term cancer is used to describe all cancerous disease states applicable to treatment according to the present invention and embraces or encompasses the pathological process associated with all virtually all epithelial cancers, including carcinomas, malignant hematogenous, ascitic and solid tumors.

Examples of cancers which may be treated using methods according to the present invention include, without limitation, carcinomas (e.g. squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas. See, for example, The Merck Manual of Diagnosis and Therapy, 17.sup.th ed. (Whitehouse Station, N.J.: Merck Research Laboratories, 1999) 973-74, 976, 986, 988, 991).

In addition to the treatment of ectopic cancers as described above, the present invention also may be used preferably to treat eutopic cancers such as choriocarcinoma, testicular choriocarcinoma, non-seminomatous germ cell testicular cancer, placental cancer (trophoblastic tumor) and embryonal cancer, among others.

The term "neoplasia" refers to the uncontrolled and progressive multiplication of tumor cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumor cells having the unique trait of loss of normal controls, resulting in unregulated growth, lack of differentiation, local tissue invasion, and/or metastasis.

As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g. squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g. gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991.

The term "additional anticancer agent" means chemotherapeutic agents such as an agent selected from the group consisting of microtubule-stabilizing agents, microtubule-disruptor agents, alkylating agents, antimetabolites, epidophyllotoxins, antineoplastic enzymes, topoisomerase inhibitors, inhibitors of cell cycle progression, and platinum coordination complexes. These may be selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate $[C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafamib, BMS-214662, tipifamib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diflitox,gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

A "PARP inhibitor" includes, but is not limited to, one or more compositions selected from the group consisting of NU1025; 3-aminobenzamide; 4-amino-1,8-naphthalimide; 1,5-isoquinolinediol; 6(5H)-phenanthriddinone; 1,3,4,5,-tetrahydrobenzo(c)(1,6)- and (c)(1,7)-naphthyridin-6 ones; adenosine substituted 2,3-dihydro-1H-isoindol-1-ones; AG14361; AG014699; 2-(4-chlorophenyl)-5-quinoxalinecarboxamide; 5-chloro-2-[3-(4-phenyl-3,6-dihydro-1 (2H)-pyridinyl)propyl]-4(3H)-quinazolinone; isoindolinone derivative INO-1001; 4-hydroxyquinazoline; 2-[3-[4-(4-chlorophenyl) 1-piperazinyl]propyl]-4-3(4)-quinazolinone; 1,5-dihydroxyisoquinoline (DHIQ); 3,4-dihydro-5 [4-(1-piperidinyl)(butoxy)-1(2H)-isoquinolone; CEP-6800; GB-15427; PJ34; DPQ; BS-201; AZD2281 (Olaparib); BS401; CHP101; CHP102; INH2BP; BSI201; BSI401; TIQ-A; an imidazobenzodiazepine; 8-hydroxy-2-methylquinazolinone (NU1025), CEP 9722, MK 4827, LT-673; 3-aminobenzamide; Olaparib (AZD2281); ABT-888 (Veliparib); BSI-201 (Iniparib); Rucaparib (AG-014699); INO-1001; A-966492; PJ-34; and the PARP1 inhibitors described in U.S. patent application Ser. No. 12/576,410.

The terms "radiotherapy" and "radiation therapy" are used interchangeably and describe therapy for cancer, especially including colon cancer, which may be used in conjunction with the present methods of treatment and formulations which exhibit synergistic anticancer activity. Radiation therapy uses high doses of radiation, such as X-rays, to destroy cancer cells. The radiation damages the genetic material of the cells so that they cannot grow. Although radiation damages normal cells as well as cancer cells, the normal cells can repair themselves and function, while the cancer cells cannot.

Radiation therapy may be used in combination with the presently claimed methods of treatment and formulations, which inhibit a cancer cells' ability to repair damage done by the radiation, thus potentiating radiation therapy. Radiation therapy is most effective in treating cancers that have not spread (metastasized). But it also may be used if the cancer has spread to nearby tissue. Radiation is sometimes used after surgery to destroy any remaining cancer cells and to relieve pain from metastatic cancer.

Radiation is delivered in one of two ways: External-beam radiation therapy and branchytherapy. External-beam radiation therapy uses a large machine to aim a beam of radiation at the tumor. After the area of cancer is identified, an ink tattoo no bigger than a pencil tip is placed on the skin of the subject so that the radiation beam can be aimed at the same spot for each treatment. This helps focus the beam on the cancer to protect nearby healthy tissue from the radiation. External radiation treatments usually are done 5 days a week for 4 to 8 weeks or more. If cancer has spread, shorter periods of treatment may be given to specific areas to relieve pain.

There are basically three types of external radiation therapy: conformal radiotherapy (3D-CRT), intensity-modulation radiation therapy (IMRT) and proton therapy. Conformal radiotherapy uses a three-dimensional planning system to target a strong dose of radiation to the cancer. This helps to protect healthy tissue from radiation. Intensity-modulated radiation therapy uses a carefully adjusted amount of radiation. This protects healthy tissues more than conformal radiotherapy does. Proton therapy uses a different type of energy (protons) than X-rays. This approach allows a higher amount of specifically directed radiation, which protects nearby healthy tissues the most. Sometimes proton therapy is combined with X-ray therapy.

Brachytherapy, or internal radiation therapy, uses dozens of tiny seeds that contain radioactive material. It may be used preferably to treat early-stage prostate and other cancer which is localized. Needles are used to insert the seeds through the skin into tissue, most often the prostate. The surgeon uses ultrasound to locate the tissue and guide the needles. As the needles are pulled out, the seeds are left in place. The seeds release radiation for weeks or months, after which they are no longer radioactive. The radiation in the seeds can't be aimed as accurately as external beams, but they are less likely to damage normal tissue. After the seeds have lost their radioactivity, they become harmless and can stay in place.

Radiation therapy may combine brachytherapy with low-dose external radiation. In other cases, treatment combines surgery with external radiation. In the present invention, compounds which are otherwise claimed may be used as radiation sensitizers to enhance or potentiate the effect of radiation by inhibiting the ability of the cancer tissue to repair the damage done by the radiation therapy.

A "substantially purified α-anomer" means that at least 99%, 98%, 97%, 96%, 95%, 94%, 93%, 92%; 91%, 90%, 89%, 88%, 87%, 86%, 85%, 84%, 83%, 82%, 81% or 80% of a nucleoside or nucleoside analog is present in α-anomer form. A "substantially purified β-anomer" means that at least 99%, 98%, 97%, 96%, 95%, 94%, 93%, 92%, 91%, 90%, 89%, 88%, 87%, 86%, 85%, 84%, 83%, 82%, 81% or 80% of a nucleoside or nucleoside analog is present in β-anomer form.

Formulations of the invention may include a pharmaceutically acceptable diluent, carrier, solubilizer, emulsifier, preservative and/or adjuvant. Acceptable formulation materials preferably are nontoxic to recipients at the dosages and concentrations employed. The pharmaceutical formulations may contain materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, polyethylene glycol (PEG), sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMACEUTICAL SCIENCES, 18.sup.th Edition, (A. R. Gennaro, ed.), 1990, Mack Publishing Company.

Optimal pharmaceutical formulations can be determined by one skilled in the art depending upon, for example, the intended route of administration, delivery format and desired dosage. See, for example, REMINGTON'S PHARMACEUTICAL SCIENCES, Id. Such formulations may influence the physical state, stability, rate of in vivo release and rate of in vivo clearance of the antibodies of the invention.

Primary vehicles or carriers in a pharmaceutical formulation can include, but are not limited to, water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical formulations can comprise Tris buffer of about pH 7.0-8.5, or acetate buffer of about pH 4.0-5.5, which may further include sorbitol or a suitable substitute. Pharmaceutical formulations of the invention may be prepared for storage by mixing the selected composition having the desired degree of purity with optional formulation agents (REMINGTON'S PHARMACEUTICAL SCIENCES, Id.) in the form of a lyophilized cake or an aqueous solution. Further, the formulations may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 5 to about 8.

The pharmaceutical formulations of the invention can be delivered parenterally. When parenteral administration is contemplated, the therapeutic formulations for use in this invention may be in the form of a pyrogen-free, parenterally acceptable aqueous solution. Preparation involves the formulation of the desired immunomicelle, which may provide controlled or sustained release of the product which may then be delivered via a depot injection. Formulation with hyaluronic acid has the effect of promoting sustained duration in the circulation.

Formulations may be formulated for inhalation. In these embodiments, a stealth immunomicelle formulation is formulated as a dry powder for inhalation, or inhalation solutions may also be formulated with a propellant for aerosol delivery, such as by nebulization. Pulmonary administration is further described in PCT Application No. PCT/US94/001875, which describes pulmonary delivery of chemically modified proteins and is incorporated by reference.

Formulations of the invention can be delivered through the digestive tract, such as orally. The preparation of such pharmaceutically acceptable compositions is within the skill of the art. Formulations disclosed herein that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized Additional agents can be included to facilitate absorption. Diluents, flavorings, low melting point waxes, vegetable oils, lubricants, suspending agents, tablet disintegrating agents, and binders may also be employed.

A formulation may involve an effective quantity of a micropoarticle containing formulation as disclosed herein in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

Once the formulation of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

Administration routes for formulations of the invention include orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. The pharmaceutical formulations may be administered by bolus injection or continuously by infusion, or by implantation device. The pharmaceutical formulations also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

Preferred methods of treatment and pharmaceutical formulations include the following.

In one embodiment, the invention provides a method of treating a subject who suffers from a cancer selected from the group consisting of colorectal cancer (CRC), breast cancer, ovarian cancer, glioblastoma multiform (GBM), melanoma, lung cancer and a glioma, the method comprising co-administering to the subject a pharmaceutically-effective amount of (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR).

In certain embodiments, the subject is treated concomitantly by radiotherapy and is optionally treated with a radiosensitizer prior to or during radiotherapy.

In certain embodiments, the subject suffers from a treatment-resistant cancer selected from the group consisting of metastatic colorectal cancer (mCRC), breast cancer in which BRCA1-deficient cells exhibit decreased sensitivity to PARP inhibitors, ovarian cancer which is resistant to platinum-containing anti-neoplastic drugs, hormone and castration-resistant prostate cancer, metastatic melanoma, drug resistant childhood acute lymphoblastic leukemia (ALL), and chemotherapy and radiotherapy-resistant glioblastomas, cervical cancer, esophageal cancer (EC), breast cancers and non-small cell lung cancer.

In certain embodiments, a subject who suffers from colorectal cancer (CRC) or metastatic colorectal cancer (mCRC) is treated with a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) an EGFR-directed treatment (e.g. co-administration of cetuximab and panitumumab).

In certain embodiments, a subject who suffers from a cancer (e.g. colorectal cancer) is treated with a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) a PARP inhibitor selected from the group consisting of NU1025; 3-aminobenzamide; 4-amino-1,8-naphthalimide; 1,5-isoquinolinediol; 6(5H)-phenanthriddinone; 1,3,4,5,-tetrahydrobenzo(c)(1,6)- and (c)(1,7)-naphthyridin-6 ones; adenosine substituted 2,3-dihydro-1H-isoindol-1-ones; AG14361; AG014699; 2-(4-chlorophenyl)-5-quinoxalinecarboxamide; 5-chloro-2-[3-(4-phenyl-3,6-dihydro-1 (2H)-pyridinyl)propyl]-4(3H)-quinazolinone; isoindolinone derivative INO-1001; 4-hydroxyquinazoline; 2-[3-[4-(4-chlorophenyl) 1-piperazinyl]propyl]-4-3 (4)-quinazolinone; 1,5-dihydroxyisoquinoline (DHIQ); 3,4-dihydro-5 [4-(1-piperidinyl)(butoxy)-1(2H)-isoquinolone; CEP-6800; GB-15427; PJ34; DPQ; BS-201; AZD2281 (Olaparib); BS401; CHP101; CHP102; INH2BP; BSI201; BSI401; TIQ-A; an imidazobenzodiazepine; 8-hydroxy-2-methylquinazolinone (NU1025), CEP 9722, MK 4827, LT-673; 3-aminobenzamide; Olaparib (AZD2281; ABT-888 (Veliparib); BSI-201 (Iniparib); Rucaparib (AG-014699); INO-1001; A-966492; PJ-34; and the PARP1 inhibitors described in U.S. patent application Ser. No. 12/576,410.

One preferred embodiment provides a method of treating a subject who suffers from BRCA-associated or refractive breast or ovarian cancer, the method comprising co-administering to the subject a pharmaceutically-effective amount of:

(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) one or more additional anti-cancer agents selected from the group consisting of a chemotherapeutic agent, a HER antibody, an antibody directed against a tumor associated antigen, an anti-hormonal compound, a cardioprotectant, a cytokine, an EGFR-targeted drug, an anti-angiogenic agent, a tyrosine kinase inhibitor, a COX inhibitor, a non-steroidal anti-inflammatory drug, a farnesyl transferase inhibitor, an antibody that binds oncofetal protein CA 125, HER2 vaccine, HER targeting therapy, Raf or ras inhibitor, doxorubicin (e.g. liposomal doxorubicin), topotecan, taxane, a dual tyrosine kinase inhibitor, TLK286 and EMD-7200, Rucaparib and a PARP inhibitor.

Another preferred embodiment provides a method of treating a subject who suffers from colorectal cancer or mCRC, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR);
(b) Regorafenib (BAY 73-4506); and
(c) optionally, radiotherapy (which may include administration of a radiosensitizer prior to or during radiotherapy).

Another preferred embodiment provides a method of treating a subject who suffers from one or more cancers selected from the group consisting of breast cancer, colorectal cancer, glioblastoma multiform (GBM) and melanoma, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) Veliparib and, optionally, one or more additional PARP inhibitors.

Still another preferred embodiment provides a method of treating a subject who suffers from one or more cancers selected from the group consisting of breast cancer, colorectal cancer, glioblastoma multiform (GBM) and melanoma, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR);
(b) Veliparib and, optionally, one or more additional PARP inhibitors; and
(c) optionally, radiotherapy (which may include administration of a radiosensitizer prior to or during radiotherapy).

Another preferred embodiment provides a method of treating a subject who suffers from pancreatic ductal adenocarcinoma (PDAC), the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) at least one additional anti-cancer agent selected from the group consisting of folinic acid, irinotecan and oxaliplatin.

Another preferred embodiment provides a method of treating a subject who suffers from colorectal cancer or mCRC, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) at least one additional anti-cancer agent selected from the group consisting of (1) oxaliplatin and/or irinotecan (2) an anti-VEGF-A antibody including but not limited to bevacizumab (3) an anti-epidermal growth factor receptor (anti-EGFR) antibody including but not limited to cetuximab and panitumumab (4) an anti-angiogenic multikinase inhibitor including but not limited to regorafenib (5) an anti-angiogenic compound including but not limited to aflibercept (6) leucovorin.

Another preferred embodiment provides a method of treating a subject who suffers from colorectal cancer or mCRC, the method comprising co-administering intravenously to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) at least one additional anti-cancer agent selected from the group consisting of (1) oxaliplatin and/or irinotecan and (2) leucovorin.

Another preferred embodiment provides a method of treating a subject who suffers from resectable esophageal cancer (EC), squamous cell carcinoma (SCC) or adenocarcinoma (AC), the method comprising co-administering intravenously to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) at least one additional anti-cancer agent selected from the group consisting of cisplatin and taxane.

Another preferred embodiment provides a method of treating a subject who suffers from colorectal hepatic metastasis, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) at least one additional anti-cancer agent selected from the group consisting of bevacizumab or cetuximab.

Another preferred embodiment provides a method of treating a subject who suffers from head and neck cancer, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) at least one additional anti-cancer agent selected from the group consisting of cisplatin, bleomycin and paclitaxel.

Another preferred embodiment provides a method of treating a subject who suffers from gastric cancer, the method comprising co-administering to the subject a pharmaceutically-effective amount of (1) 5-formyl-2'-deoxyuridine (fdU), optionally in combination with 5-hydroxy-2'-deoxyuridine (hUdR) and (2) S-1.

Another preferred embodiment provides a method of treating a subject who suffers from triple-negative breast cancer (TNBC), the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) at least one additional anti-cancer agent selected from the group consisting of cyclophosphamide and methotrexate.

Another preferred embodiment provides a method of treating a subject who suffers from a solid tumor, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) MK-4827 and, optionally, one or more additional PARP inhibitors.

The subject treated in the embodiment of the preceding paragraph may suffer from one or more cancers selected from the group consisting of colorectal cancer (CRC), metastatic colorectal cancer (mCRC), breast cancer, ovarian cancer, non-small-cell lung cancer and prostate cancer.

In certain embodiments, a subject treated by the methods of treatment of the invention suffers from one or more cancers selected from the group consisting of relapsed or refractory T-cell prolymphocytic leukemia (T-PLL), chronic lymphocytic leukemia (CLL), locally advanced or metastatic colorectal carcinoma (CRC), persistent or recurrent endometrial carcinoma, locally advanced or metastatic triple negative or highly proliferative estrogen receptor positive (ER+) breast cancer and partially platinum-sensitive epithelial ovarian cancer.

Another preferred embodiment provides a method of treating a subject who suffers from a solid tumor, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU) and/or 5-hydroxy-2'-deoxyuridine (hUdR); and
(b) MK-4827, carboplatin and, optionally, one or more additional PARP inhibitors.

Still another preferred embodiment provides a method of treating a subject who suffers from an advanced solid tumor, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) CEP-9722 and, optionally, one or more additional PARP inhibitors.

Another preferred embodiment provides a method of treating a subject who suffers from melanoma, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) temozolomide in combination with E7016 and/or INO-1001 and, optionally, one or more additional PARP inhibitors.

Another preferred embodiment provides a method of treating a subject who suffers from metastatic germline BRCA mutated breast cancer, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) BMN-673 and, optionally, one or more additional PARP inhibitors.

Still another preferred embodiment provides a method of treating a subject who suffers from metastatic breast cancer and/or ovarian cancer, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) Rucaparib and, optionally, one or more additional PARP inhibitors.

Another preferred embodiment provides a method of treating a subject who suffers from metastatic melanoma and/or breast cancer, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) CEP 9722 and, optionally, one or more additional PARP inhibitors.

Another preferred embodiment provides a method of treatment comprising treating a subject who suffers from non-small-cell lung cancer (NSCLC), the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) Veliparib (ABT-888) and, optionally, one or more additional PARP inhibitors.

Another preferred embodiment provides a method of treating a subject who suffers from one or more cancers selected from the group consisting of breast cancer, colorectal cancer, glioblastoma multiform (GBM) and melanoma, the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) 3-aminobenzamide and, optionally, one or more additional PARP inhibitors.

Another preferred embodiment provides a method of treating a subject who suffers from recurrent locoregional disease and/or metastatic squamous cell carcinoma of the head and neck (SCCHN), the method comprising co-administering to the subject a pharmaceutically-effective amount of:
(a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
(b) cetuximab and one or more platinum-based antineoplastic drugs (e.g. Cisplatin, Carboplatin, Oxaliplatin, Satraplatin, Picoplatin, Nedaplatin, Triplatin tetranitrate, and Lipoplatin).

One example of a pharmaceutical formulation of the invention comprises a pharmaceutically-effective amount of:
(a) (1) 5-FU, a 5-fluorouracil (FU) prodrug or a 5-FU metabolite and (2) 5-formyl-2'-deoxyuridine (fdU) or a 5-formyl-2'-deoxyuridine (fdU) derivative, optionally in combination with 5-hydroxy-2'-deoxyuridine (hUdR);
(b) optionally, one or more platinum-based antineoplastic drugs (e.g. Cisplatin, Carboplatin, Oxaliplatin, Satraplatin, Picoplatin, Nedaplatin, Triplatin tetranitrate, and Lipoplatin);
(c) optionally, one or more additional anti-cancer drugs (e.g. a PARP inhibitor); and
(d) optionally, a pharmaceutically-acceptable excipient.

These and other aspects of the invention are illustrated further in the following non-limiting Examples.

Example 1

Synergistic Interaction Between Deoxyuridine Analogs and 5-FU in a Cancer Cell-Specific Manner.
In Example 1, all references to Figures relate to FIGS. 1-9. A reference to "FIG. 1A" means FIG. 1, Panel A.
Experimental Summary 5-Fluorouracil (5-FU) is a halogenated nucleobase analog that is widely used in chemotherapy. We have shown that 5-hydroxymethyl-2'-deoxyuridine (hmUdR) synergistically enhances the activity of 5-FU in cell lines derived from solid tumors but not normal tissues. While the cytotoxicity of 5-FU and hmUdR was not directly related to the amount of the modified bases incorporated into cellular DNA, incubation with this combination resulted in dramatic increase in the number of single strand breaks in replicating cancer cells, leading to NAD-depletion as consequence of poly (ADP-ribose) synthesis and S phase arrest. Cell death resulting from the base/nucleoside combination did not occur by apoptosis, autophagy or necroptosis. Instead, the cells die via necrosis as a result of NAD depletion. The 5-FU-related nucleoside analog, 5-fluoro-2'-deoxyuridine, also displayed synergy with hmUdR, whereas hmUdR could not be replaced by 5-hydroxymethyluracil. Among other 5-modified deoxyuridine analogs tested, 5-formyl-2'-deoxyuridine and, to a lesser extent, 5-hydroxy-2'-deoxyuridine, also acted synergistically with 5-FU, whereas 5-hydroxyethyl-2'-deoxyuridine did not. Together, our results revealed an unexpected synergistic interaction between deoxyuridine analogs and 5-FU in a cancer cell-specific manner, and suggested that these novel base/nucleoside combinations could be developed into improved 5-FU-based chemotherapies. See U.S. Pat. No. 8,617,540.

Materials and Methods
Chemicals

Quinolyl-valyl-O-methylaspartyl-[-2,6-difluorophenoxy]-methyl ketone (QVD) was obtained from R&D Systems. LY294002 and TRAIL were purchased from Cayman Chemical and PeproTech, respectively. Caffeine was obtained from USB. ABT-888 was purchased from Enzo Life Sciences. 5-formyl-2'-deoxyuridine was synthesized and purified as previously described (11). All other chemicals were obtained from Sigma-Aldrich.

Cell Culture

HT-29 (derived from colorectal adenocarcinoma) and PANC-1 cells (derived from pancreatic carcinoma) were cultured in 4.5 g/l glucose-containing DMEM supplemented with 10% fetal bovine serum (FBS), 100 units/ml penicillin, 100 µg/ml streptomycin and 2 mM glutamine. HCT 116 cells (derived from colorectal carcinoma) were cultured in McCoy's 5A medium supplemented with 10% FBS, 100 units/ml penicillin, 100 µg/ml streptomycin and 2 mM glutamine. EKVX cells (derived from lung adenocarcinoma) were cultured in RPMI medium supplemented with 10% FBS, 100 units/ml penicillin, 100 µg/ml streptomycin and 2 mM glutamine. WI-38 cells (derived from normal lung fibroblast) were cultured in 4.5 g/l glucose-containing DMEM supplemented with 20% FBS, 100 units/ml penicillin, 100 µg/ml streptomycin and 2 mM glutamine, 1 mM pyruvate and 1× vitamin solution (Invitrogen). Human umbilical vein endothelial cells (HUVEC) were obtained from Genlantis and cultured in the endothelial cell growth medium supplied by Genlantis. All the cells were maintained in 5% $CO_2$ at 37° C. SID507 and SID509 cells (untransformed colonocytes isolated from an individual with familial adenomatous polyposis by M. Clapper and obtained from the Cell Culture Facility at Fox Chase Cancer Center) were cultured in 4.5 g/l glucose-containing DMEM supplemented with 15% FBS, 100 units/ml penicillin, 100 µg/ml streptomycin and 2 mM glutamine and 1 mM pyruvate.

Colony Formation Assay

HT-29 cells were seeded at $6 \times 10^4$ cells/well in 6-well plates, and on the next day, indicated compounds were added (0.5 µM for 5-FU, 5 µM for hmUdR). After incubation for indicated time periods (0, 24, 48 or 72 h), cells were trypsinized, washed and replated into 6 cm dishes using appropriate dilutions and then incubated for 10 days without drugs. Colonies were stained with 0.25% methylene blue/30% ethanol, and counted. All assays were carried out in triplicate.

Comet Assay

HT-29 cells were seeded at $4 \times 10^5$ cells/well in 6-well plates, and on the next day, indicated nucleosides and/or bases were added (0.5 µM for 5-FU, 5 µM for hmUdR). After incubation for indicated time periods (12-48 h), the cells were trypsinized and washed in PBS. For time course experiments, cells harvested at each time point were stored in 10% DMSO/40% DMEM/50% FBS at −80° C. until slide processing. Approximately 5,000 cells were spread in 0.9% low-melting point agarose/PBS on CometSlide (Trevigen), and chilled at 4° C. in the dark for 20 min.

For alkaline comet assay, slides were soaked in precooled lysis buffer containing 2.5 M NaCl/100 mM EDTA/10 mM Tris/1% sarkosyl/1% Triton X-100 at 4° C. for 45 min, followed by soaking in precooled 300 mM NaOH/1 mM EDTA at 4° C. for 45 min. Subsequently, slides were electrophoresed in 300 mM NaOH/1 mM EDTA at 1.4 V/cm for 20 min at 4° C., washed in 70% ethanol for 5 min, and allowed to dry in the dark. Cellular DNA was stained with 1×SYBR Green I (Molecular Probes) 30 min before analysis with a fluorescence microscope. Alkaline comet assays were performed in triplicate and more than 30 comets for each condition were photographed at the Light Microscope Facility at Fox Chase Cancer Center, and analyzed by CometScore software (TriTek).

For neutral comet assay, slides were soaked in precooled lysis buffer at 4° C. for 30 min, followed by washing in precooled 1×TBE buffer (90 mM Tris-borate, pH8.3, 2 mM EDTA). Slides were electrophoresed in 1×TBE buffer at 2 V/cm for 20 min at 4° C., rinsed in deionized water, washed in 70% ethanol for 5 min, and allowed to dry in the dark. Subsequently, slides were processed as above for DNA staining and comet analyses. Neutral comet assays were conducted in duplicate, in each of which more than 60 comets for each condition were analyzed.

Quantitation of 5-FU and hmUdR Incorporated into Cellular DNA

[6-$^3$H]-5-FU (18 Ci/mmol) and of [$^3$H]-hmUdR (10 Ci/mmole) were purchased from Moravek Biochemicals. HT-29 cells were seeded at 5×10$^5$ cells/well (for treatment with one compound only) or 10×10$^5$ cells/well (for treatment with 5-FU and hmUdR) in 6-well plates one day before drug addition. For 5-FU quantitation, 0.5 µM 5-FU and 5 µCi/well of [6-$^3$H]-5-FU were added to the medium together with or without 5 µM nonradioactive hmUdR in triplicate. For hmUdR quantitation, 5 µM hmUdR and 1 µCi/well of [$^3$H]-hmUdR were added to the medium together with or without 0.5 µM nonradioactive 5-FU in triplicate. At 24 or 48 h after drug addition, cells were washed with PBS and their DNA was recovered with Trizol (Invitrogen) according to the manufacturer's instruction. Subsequently the recovered DNA was quantitated by 260 nm absorbance, and its radioactivity was measured by liquid scintillation counting.

Synchronization of Cultured Cells at the $G_1$/S Boundary

HT-29 cells that were seeded at 2×10$^6$ cells/plate in 10 cm dishes and incubated with 20 ng/ml nocodazole for 18 h. After washing with PBS, 1 µg/ml aphidicolin and, where indicated, 0.5 µM 5-FU and 5 µM hmUdR were added for 12 h. The synchronized cells were washed with PBS prior to the addition of fresh medium containing the indicated nucleosides and/or bases.

Cell Cycle Analysis

Cells grown in 10 cm dishes were trypsinized, spun down and suspended in 10 ml PBS containing 0.5% FBS. After centri5-FUgation, the cells were resuspended in 0.5 ml PBS/0.5% FBS, and fixed in 5 ml 70% ethanol at −20° C. After centri5-FUgation and washing with 10 ml PBS/0.5% FBS, the cells were suspended in 1.5 ml PBS/0.5% FBS containing 10 µg/ml propidium iodide and 50 µg/ml RNase A, and incubated at 37° C. for 30 min. Cell cycle distribution was analyzed with a FACScan flow analyzer (Becton Dickinson).

Time-Lapse Image Acquisition

HT-29 cells were infected with a retroviral vector for expression of GFP-5-FUsed histone H2B. HT-29 cells expressing GFP-H2B were seeded at 2×10$^5$ cells/well in 6-well plates. On the following day, drug treatments were initiated and cell proliferation was monitored by time-lapse microscopy. Image acquisition was done at the Light Microscope Facility at Fox Chase Cancer Center using phase-contrast and GFP-specific fluorescence microscopy (Nikon TE2000S) controlled by Metamorph (Molecular Devices). Images were captured at a rate of one frame per 15 minutes for 60 hours, in which cells were kept at 37° C. Images were captured from 10 areas per well. The number of cell divisions that occurred in each area was counted for the first 24 h and the second 24 h periods.

Immunoblotting

For detection of PARP1 cleavage and autophagy-related proteins, the HT-29 cells treated as indicated were washed with PBS and resuspended in 40 mM HEPES-KOH, pH7.5/500 mM NaCl/10% glycerol/0.1% NP-40/Protease Inhibitor Cocktail III for mammalian cells (Research Products International Corp). After 10 mM on ice, cells were scraped and centri5-FUged at 16,000×g for 10 min at 4° C. The supernatant was recovered. This whole cell extract (50 µg protein) was subjected to SDS-containing polyacrylamide gel electrophoresis, and transferred to Immobilon-P membrane (Millipore). For detection of poly(ADP-ribose), the nuclear pellet was recovered after removing the whole cell extract as prepared above except that the lysis buffer was supplemented with 50 µM ethacridine, an inhibitor of poly(ADP-ribose) glycohydrolase. 10 µg protein of the nuclear pellet was subjected to gel electrophoresis and transfer to membrane as described above. Primary antibodies used in this study were anti-PARP1 monoclonal mouse antibody (Trevigen), anti-p62 polyclonal rabbit antibody (Santa Cruz Biotechnology), anti-LC3 polyclonal rabbit antibody (Novus Biologicals), anti-β-actin monoclonal mouse antibody (Sigma), and anti-PCNA monoclonal mouse antibody (PC10; Santa Cruz Biotechnology), anti-poly(ADP-ribose) mouse monoclonal antibody (Tulip Biolabs). As secondary antibodies, either IRDye800CW-conjugated anti-mouse IgG antibody, IRDye700-conjugated anti-rabbit IgG antibody (both from LI-COR Biotechnology) or horseradish peroxidase-conjugated anti-mouse IgG antibody (Bio-Rad Laboratories) was used. Immunoblot signals were detected either by Odyssey Imaging System (LI-COR Biotechnology) or by exposure of X-ray films to the membrane soaked in ECL reagent (GE Healthcare).

Cell Growth/Viability Assays

In the WST-1 assay measuring cell growth and viability, cells were seeded in 96-well plates at the following densities: 10,000 cells/well for HT-29; 2,500 cells/well for HCT 116; 1,000 cells/well for PANC-1; 5,000 cells/well for EKVX; 3,000 cells/well for WI-38; 3,000 cells/well for SID-507 and SID-509; 2,000 cells/well for HUVECs. Indicated concentrations of drugs were added to wells one day after seeding. After three days incubation with the indicated nucleosides and/or bases (except for SID-507 and -509 cells which were incubated for seven days), 5 µl WST-1 reagent (Roche) was added to each well, and plates were 5-FUrther incubated at 37° C. for 3 h. Cell proliferation was quantitated by measuring 450 nm absorbance and 600 nm as a background. All assays were performed in triplicate.

Cell proliferation assays measuring genomic DNA were carried out using the CyQUANT kit (Invitrogen). In these experiments, the cells after drug treatments were replated to grow in the absence of the drugs for six days, and their nucleic acids was quantitated by CyQUANT assay. These assays were also conducted in triplicate.

Determination of Cellular NAD Levels

Extracts of cells treated as indicated were prepared as described by Zong et al (12). Protein concentrations were measured with the BCA protein assay reagent (Pierce). NAD concentrations were determined with NAD+/NADH cell-based assay kit (Cayman Chemical) and normalized using protein concentration.

Evaluation of Drug Interactions

Parameters of an isobologram for 50% growth inhibition (GI50) were calculated from data obtained from simultaneous treatment with the two drugs by assuming that the isobole fits to a hyperbolic curve. The minimal combination index (13) for each cell line was obtained from the isobologram parameters.

Results

The Combination of 5-FU and hmUdR has a Much Greater Effect on Cell Survival than Either Agent Alone.

Although nucleoside/base analogs, such as 5-FU and gemcitabine, have been used as cancer therapeutics for many years, there have been relatively few efforts to examine the activity of combinations of nucleoside analogs. In initial studies, we focused on hmUdR, a derivative of thymidine generated by ionizing radiation that is cytotoxic when added to cancer cells cultured in vitro (6-9). The combination of 5-FU and hmUdR markedly reduced colony formation in p53 mutant colorectal adenocarcinoma HT-29 cells compared with either compound alone, suggesting that these compounds together synergistically increase cytotoxicity (FIG. 1A). Colony formation was reduced by about 50% after incubation with 5-FU and hmUdR for 24 h and by more than 95% after incubation for 48 h (FIG. 1B).

Effects of 5-FU and hmUdR on the Integrity of Genomic DNA

Figure 7:
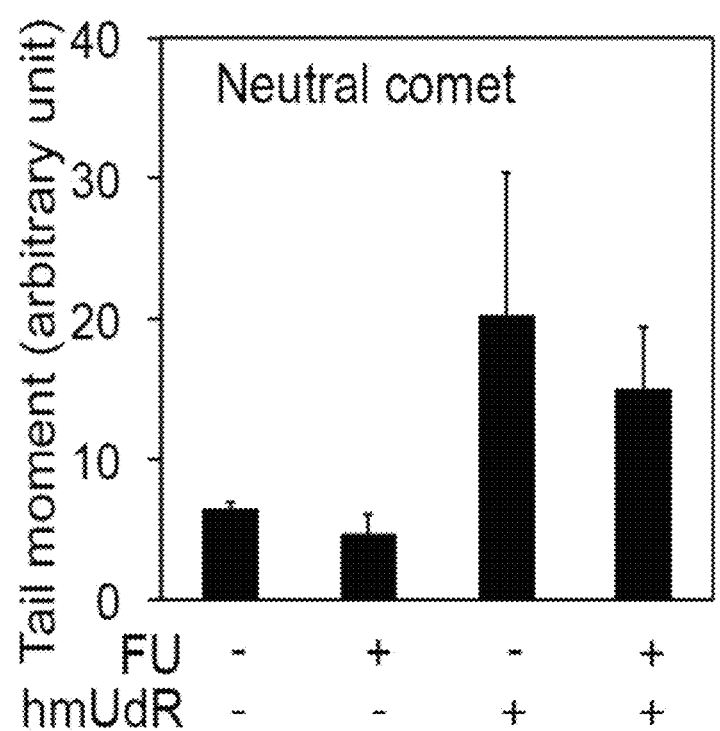
FIG. 7. Neutral comet assays for detection of double-strand breaks (DSBs) in HT-29 cells treated for 48 h with indicated combinations of 0.5 μM FU and 5 μM hmUdR.

To gain insights into the mechanisms underlying the apparent synergistic activity of 5-FU and hmUdR, we examined genome integrity using single cell gel electrophoresis (comet) assays under alkaline conditions. While incubation with either 5-FU or hmUdR did not significantly increase the number of single-strand breaks, there was a dramatic increase in the number of DNA single strand breaks when HT-29 cells were incubated with both 5-FU and hmUdR (FIG. 1C). As expected, the number of strand breaks increased with increasing time of incubation with the combination of 5-FU and hmUdR (FIG. 1D). In contrast, the number of double strand breaks measured in a neutral comet assay increased when cells were incubated with hmUdR whereas 5-FU has no significant effect on DNA double strand break formation in either absence or presence of hmUdR (FIG. 7). Thus we conclude that the increase in the number of single- but not double-strand breaks in genomic DNA correlates with the enhanced cytotoxicity of the 5-FU and hmUdR combination.

Figure 8:
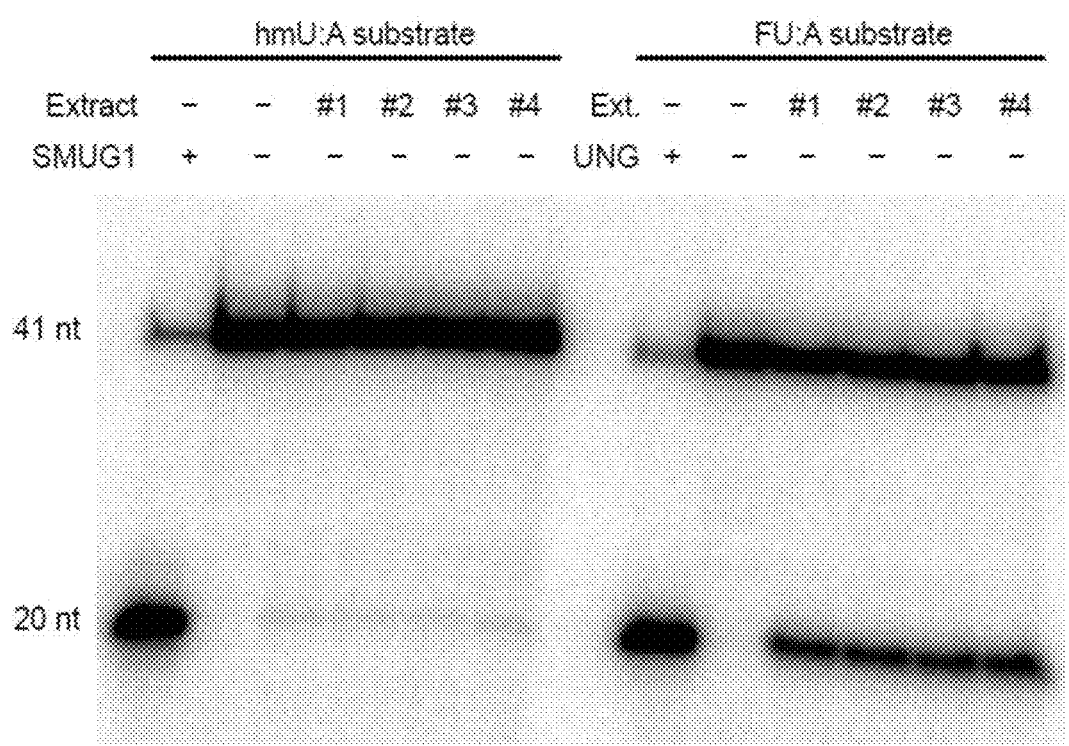
FIG. 8. Base excision activity of HT-29 cell extract. 124 fmol of double-stranded oligonucleotide containing an hmU:A or FU:A pair was incubated at 37° C. for 1 h with either an indicated recombinant enzyme or 10 μg protein of the following whole cell extracts: #1 from untreated cells; #2 from the cells treated with 0.5 μM FU for 48 h; #3 from the cells treated with 5 μM hmUdR for 48 h; #4 from the cells treated with 0.5 μM FU and 5 μM hmUdR for 48 h. After incubation, the oligonucleotides were treated with 1 N NaOH at 90° C. for 5 min, neutralized with 1 M acetic acid, and subjected to 20% sequencing gel electrophoresis. 41 nt, uncleaved substrate; 20 nt, product cleaved at hmU or FU site after damage-specific DNA glycosylase reaction.

To determine whether either 5-FU or hmUdR modulates the incorporation of the other compound into cellular DNA, we measured the incorporation of tritium-labeled derivatives of 5-FU and hmUdR in the absence or presence of the other compound. As shown in FIGS. 1E and F, incorporation of 5-FU was not stimulated by the presence of hmUdR nor vice versa. The incorporation of hmUdR estimated here appears much higher than the incorporation of hmUdR previously measured in U2OS cells (14). This is probably because HT-29 cells have extremely weak activity for excision of hmU (FIG. 8). It should be noted that incorporation of 5-FU at 48 h was decreased in the presence of hmUdR. While this may reflect increased cell death, it is clear that the increased number of single-strand breaks observed in cells incubated with the combination of 5-FU and hmUdR is not simply due to increased 5-FU or hmUdR incorporation into cellular DNA.

Figure 9:
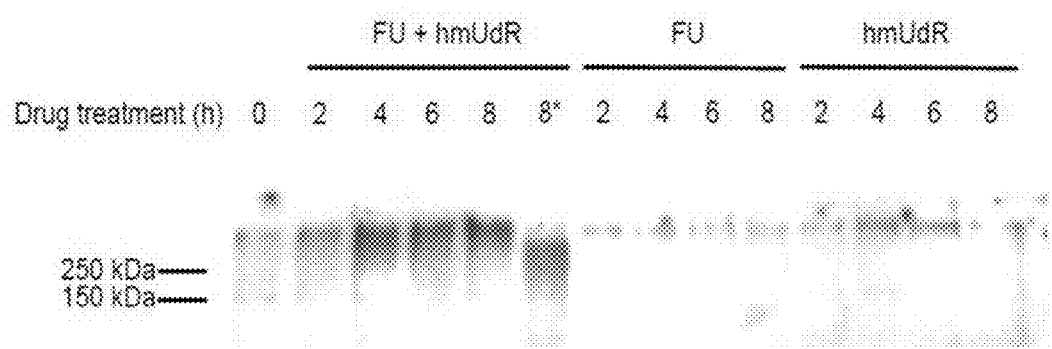
FIG. 9. Immunoblot detection of poly(ADP-ribose). HT-29 cells were treated with indicated drugs for indicated time periods and their nuclear pellets were prepared as described in Materials and Methods. All samples except the sample indicated with an asterisk were processed in the lysis buffer supplemented with 50 μM ethacridine, a poly(ADP-ribose) glycohydrolase inhibitor.

Hyperactivation of Poly (ADP-Ribose) Polymerase 1, Increased Poly (ADP-Ribose) Synthesis and NAD Depletion in Cells Incubated with the Combination of 5-FU and hmUdR The poly(ADP-ribose) polymerase, PARP1, plays a major role in the cellular response to single strand breaks (15). This enzyme binds to and is activated by single strand breaks, resulting in the synthesis of poly (ADP-ribose) chains on PARP1 itself and other proteins in the vicinity. In accord with our results showing that co-incubation with 5-FU and hmUdR results in a synergistic increase in the number of single-strand breaks, the levels of poly (ADP-ribose) were much higher in cells treated with 5-FU and hmUdR compared with either compound alone (FIG. 9). Since NAD is the substrate for poly (ADP-ribose) synthesis, it is likely that NAD levels in cells treated with 5-FU and hmUdR will be reduced. To test this idea, we measured the activity of the mitochondrial succinate-tetrazolium reductase complex that is dependent upon cellular NAD(P)/NAD(P)H levels using the WST-1 assay. As expected, incubation of cells with 5-FU and hmUdR resulted in reduced succinate-tetrazolium reductase activity (FIGS. 1G and H). This reduction in activity was partially corrected by the inhibition of poly (ADP-ribose) synthesis using PARP inhibitors, either 3-aminobenzamide (3AB, FIG. 1G) or ABT-888 (FIG. 1H). 5-FUrthermore we directly measured the cellular levels of NAD in the cells treated with 5-FU and hmUdR, and observed that the combination treatment with these compounds drastically decreased the NAD level (FIG. 1I). To examine whether PARP inhibition can restore cell proliferation and viability, we examined the effect of 5-FU and hmUdR on cell proliferation by using a CyQUANT assay that measures cellular nucleic acid (FIG. 1J). In accord with the colony forming assays, the combination of 5-FU and hmUdR dramatically reduced cell proliferation, and the PARP inhibitor, 3AB, did not rescue the effect of 5-FU and hmUdR on cell proliferation.

Effects of 5-FU and hmUdR on Cell Cycle Progression

HT-29 cells were synchronized at the $G_1/S$ boundary by sequential treatments with nocodazole and aphidicolin. 5-FU and hmUdR were added to the medium during the aphidicolin treatment and then maintained after aphidicolin removal (FIG. 2A). Although one third of the cell population remained in $G_2/M$ phase after the aphidicolin treatment due to incomplete recovery from the nocodazole treatment, the majority of both treated (61%) and untreated cells (58%) were in the $G_1$ phase and S phase cells were scarce (10% of untreated and 11% of treated cells). Following removal of aphidicolin and incubation for 12 h, 44% of untreated cells and 41% of treated cells were in S phase. By 24 h, the untreated cell population exhibited a normal cell cycle distribution with a major $G_1$ population. In contrast, the majority of treated cells remained in S phase up to 48 h after the removal of aphidicolin. To confirm that these cells are trapped in S phase, we analyzed the frequency of cell division for approximately two cell-cycle periods by time-lapse video microscopy. When untreated cells were analyzed, the number of cell divisions observed per view field during the second 24 h period was 1.6 times (±0.6) the number during the first 24 h period, indicating continued cell cycle progression. Similarly the cells treated with either 0.5 µM 5-FU or 5 µM hmUdR alone had ratios of 1.5±0.3 and 1.4±0.2, respectively. In contrast, the cells treated with both 5-FU and hmUdR divided much less frequently in the second 24 h of treatment, 0.5 times (±0.3) the number observed during the first 24 h. Thus, co-incubation with 5-FU and hmUdR results in cell cycle arrest mainly in the first S phase after the 5-FU/hmUdR addition.

To further characterize this cell cycle arrest, we examined the effects of 5-FU and hmUdR alone compared with their combination (FIG. 2B). Treatment with 5-FU alone caused cells to accumulate in S phase (52%), although to a lesser extent than after treatment with both 5-FU and hmUdR (64%) whereas hmUdR alone did not change the cell cycle distribution. Interestingly, the S phase arrest induced by 5-FU alone was abolished when cells were treated with caffeine, an ATM/ATR inhibitor, whereas the S phase arrest induced by the combination of 5-FU and hmUdR was resistant to caffeine, indicating that the cell cycle arrest induced by the combination is mechanistically distinct from that induced by 5-FU alone (FIG. 2B).

To determine whether 5-FU and hmUdR inhibit DNA replication in the absence of NAD depletion, we examined the effect of 3AB on the S phase arrest induced by 5-FU and hmUdR (FIG. 2C). Addition of 3AB simultaneously with 5-FU and hmUdR enabled most cells to progress through S phase to $G_2/M$. We also observed by alkaline comet assay that the same treatment significantly decreased the number of strand breaks compared to the cells treated without 3AB (FIG. 2D), suggesting that inhibition of PARP activation by 3AB not only enables cells to continue DNA replication but also to repair a significant fraction of, if not all, replication-dependent DNA damage caused by 5-FU and hmUdR. The accumulation of $G_2/M$ cells when incubated with 3AB in addition to 5-FU and hmUdR suggests that residual replication-dependent DNA damage activates the $G_2/M$ checkpoint. In support of this idea, the addition of caffeine partially released the $G_2/M$ arrest, resulting in the emergence of $G_1$ cells (FIG. 2C).

Mechanism of Cell Death Induced by 5-FU and hmUdR

We sought to investigate the mechanism by which cells die following the combination treatment. In initial studies, we asked whether the combination of 5-FU and hmUdR induced apoptosis. PARP1 cleavage, a characteristic of apoptosis, was induced by TRAIL and LY294002, which are known to cause apoptosis (16), but not by the 5-FU and hmUdR combination (FIG. 3A). In addition, treatment with QVD, a pan-caspase inhibitor that blocks apoptosis (17), did not diminish the growth inhibition effect of 5-FU and hmUdR as observed in either the WST-1 assay (FIG. 3B) or the CyQUANT assay (data not shown). Next we determined changes in the levels of p62 (18) and LC3-II proteins (19), which are indicative of autophagy. Alterations in these proteins were not detected in cells treated with the 5-FU and hmUdR combination (FIG. 3C). Finally we used a necroptosis-specific inhibitor, necrostatin-1 (Nec-1) (20), and found that it did not reduce the growth inhibition effect of 5-FU and hmUdR (FIG. 3D and data not shown). Together these results demonstrate that treatment of HT-29 cells with the 5-FU and hmUdR combination does not induce apoptosis, autophagy or necroptosis, and suggest that the combination of 5-FU and hmUdR induces necrosis as a consequence of PARP1-dependent NAD depletion (21).

Figure 4:
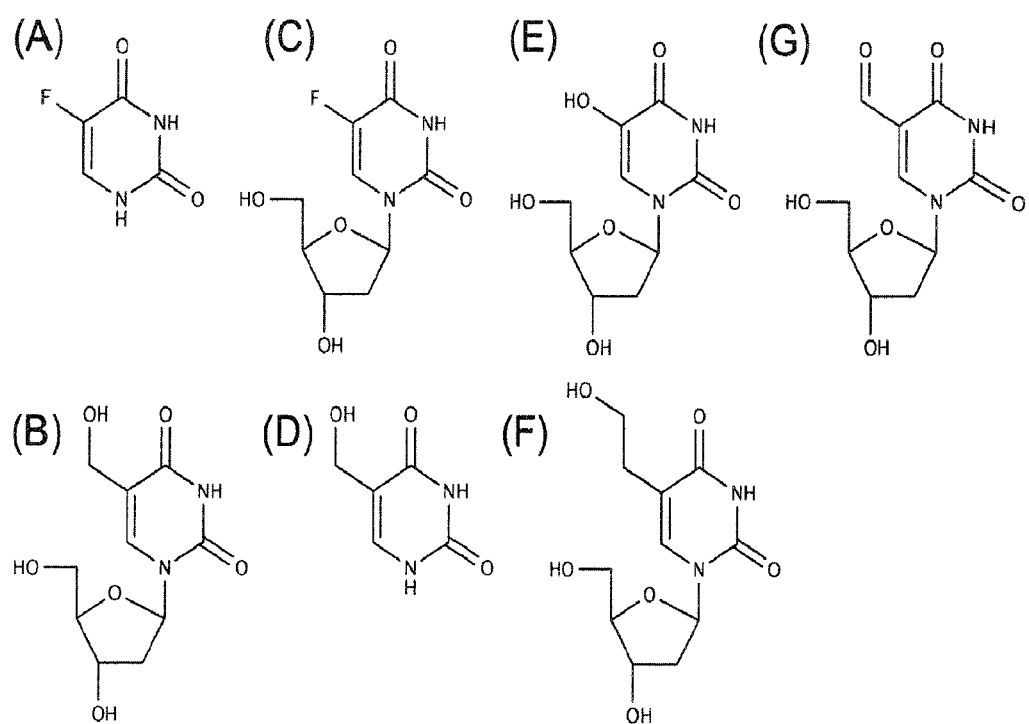
FIG. 4. Chemical structures of base/nucleoside analogs tested in this study. (A) 5-FU. (B) hmUdR. (C) 5-FUdR. (D) hmU. (E) hUdR. (F) heUdR. (G) foUdR.
Figure 5:
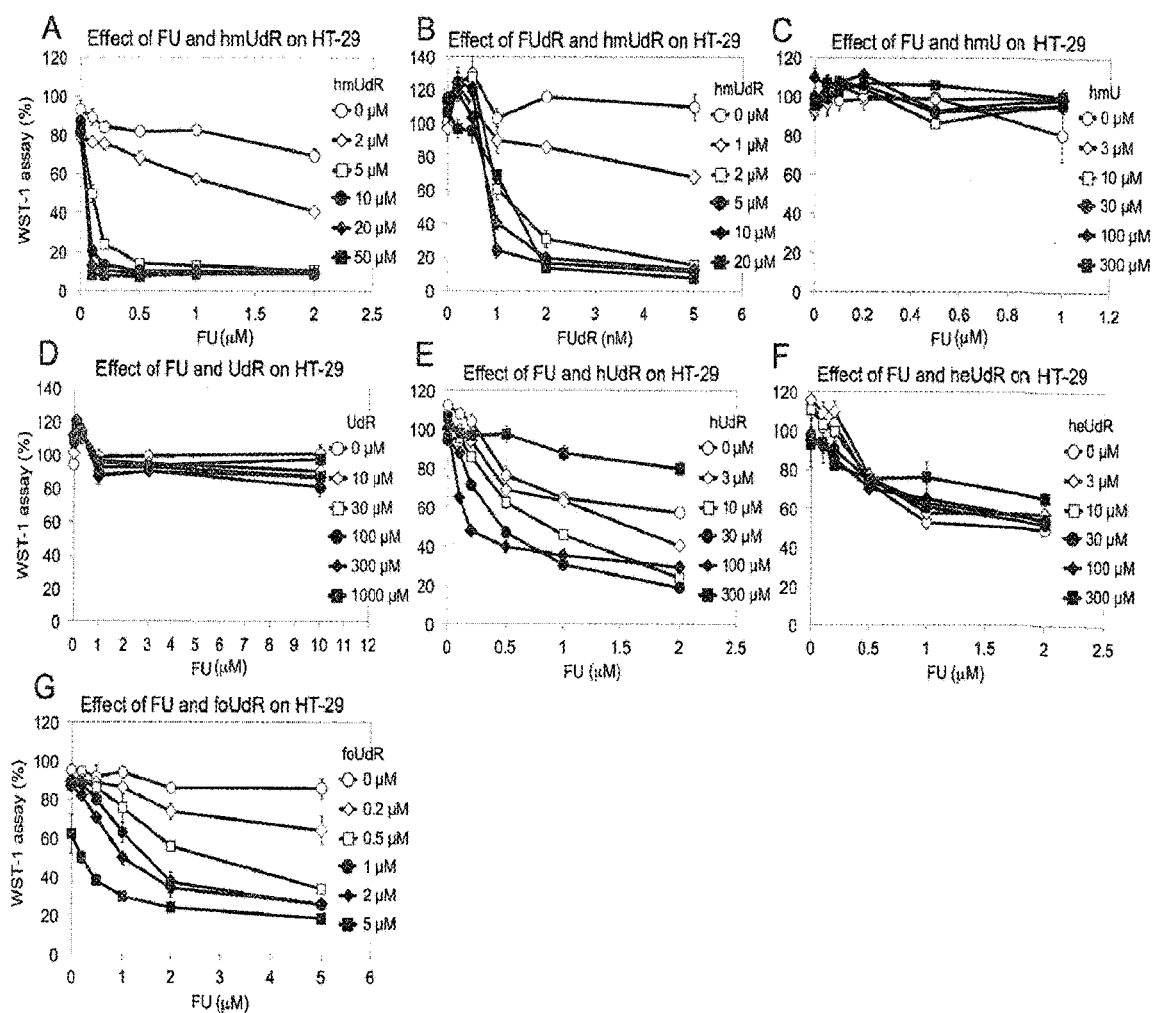
FIG. 5. Effect of various drug combinations on the growth of HT-29 cells. (A) 5-FU and hmUdR. (B) 5-fluoro-2'-deoxyuridine (5-FUdR) and hmUdR. (C) 5-FU and hmU. (D) 5-FU and 2'-deoxyuridine (UdR). (E) 5-hydroxy-2'-deoxyuridine (hUdR) and 5-FU. (F) 5-hydroxyethyl-2'-deoxyuridine (heUdR) and 5-FU. (G) 5-formyl-2'-deoxyuridine (foUdR) and 5-FU. HT-29 cells were treated with indicated compounds for 72 hours, and the cell proliferations were measured by WST-1 assay. Data are from triplicate experiments and plotted with standard deviations.
Figure 6:
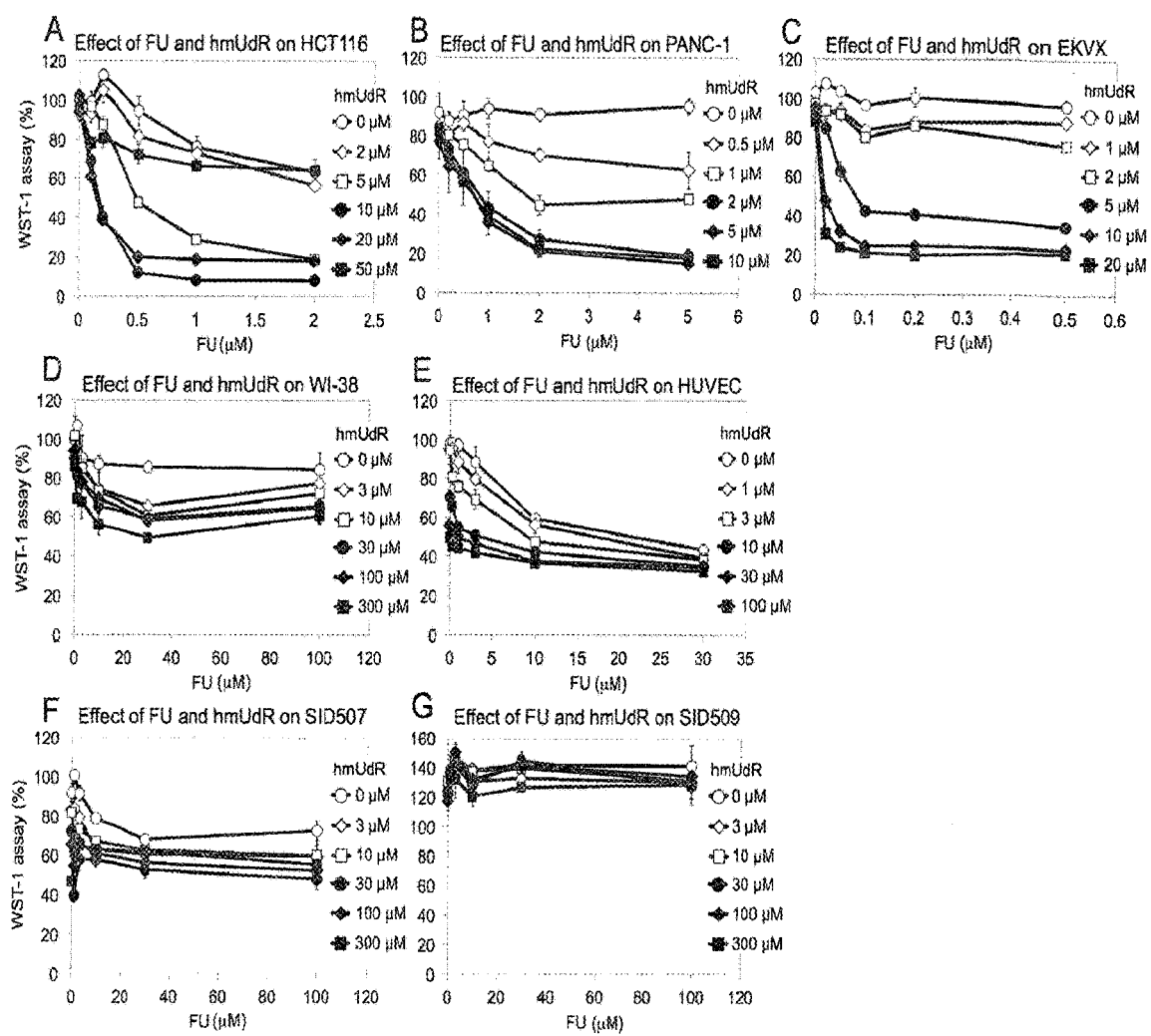
FIG. 6. Effect of 5-FU and hmUdR on the growth of various cells. (A) HCT 116 (p53-proficient colorectal carcinoma). (B) PANC-1 (pancreatic cancer). (C) EKVX (non-small cell lung cancer). (D) A normal cell line, WI-38 (embryonic lung fibroblast). (E) Human umbilical vein endothelial cells (HUVEC). These cells were treated for 72 hours with increasing concentrations of 5-FU and hmUdR, and their proliferations were measured by WST-1 assay. (F) SID507 (normal human colon cell line). (G) SID509 (normal human colon cell line). These normal colon cells were tested by the same procedures as above except that they were incubated with or without 5-FU and hmUdR for 7 days. Data are from triplicate experiments and plotted with standard deviations.

Analysis of Derivatives of 5-FU and hmUdR to Identify the Molecular Features of these Compounds that are Required for their Synergistic Activity Since results that we obtained with the WST-1 assay correlated with the number of DNA single strand breaks and cytotoxicity generated by 5-FU and hmUdR, we used this assay to determine the activity of several compounds that are structurally and/or functionally related to 5-FU or hmUdR (FIG. 4). When combined with hmUdR, the GI50 of HT-29 cells for 5-FU was drastically decreased from 19 µM to less than 0.1 µM (FIG. 5A). 5-Fluoro-2'-deoxyuridine (5-FUdR), a nucleoside derivative of 5-FU with anti-cancer activity similar to 5-FU (1), also acted synergistically with hmUdR, (FIG. 5B). In contrast, 5-hydroxymethyluracil, a base derivative of hmUdR, did not significantly enhance 5-FU activity (FIG. 5C). Four derivatives of hmUdR, 2'-deoxyuridine (UdR), 5-hydroxy-2'-deoxyuridine (hUdR), 5-hydroxyethyl-2'-deoxyuridine (heUdR), and 5-formyl-2'-deoxyuridine (foUdR) were also evaluated. Both foUdR (FIG. 5G) and, to a lesser extent, hUdR (FIG. 5E) acted synergistically with 5-FU. The activity of foUdR with 5-FU was comparable to that of hmUdR. In contrast, neither UdR nor heUdR significantly enhanced 5-FU activity (FIGS. 5D and F).

Synergistic Activity of 5-FU and hmUdR in Cancer but not Normal Cells

Since hmUdR synergistically enhances the killing of p53 mutant colon cancer cells by 5-FU, we asked whether this combination of nucleoside/base analogs has similar activity in other cancer cell lines and comparable non-malignant cell lines. First we examined another colorectal carcinoma cell line, HCT 116, that has wild type p53 but is defective in DNA mismatch repair. We obtained similar results to those of HT-29 cells except at the highest hmUdR concentration tested, 50 µM (FIG. 6A). Nonetheless, it is evident that a combination of 5-FU and up to 20 µM hmUdR synergistically inhibited the growth of colon cancer cell lines in vitro regardless of their p53 status. Cell lines derived from other tumor types were also tested for growth inhibition by 5-FU and hmUdR. PANC-1 cells from pancreas and EKVX cells from lung also showed highly synergistic responses to these compounds at relatively low concentrations (FIGS. 6B and C). In contrast, comparable normal cell lines (WI-38 lung fibroblasts, FIG. 6D; SID507 and SID509 normal human colon cell lines, FIGS. 6F and G) exhibited either no synergy with 5-FU and hmUdR or a modest degree of synergy (human umbilical vein endothelial cells [HUVECs], FIG. 6E).

To quantify the synergy of the 5-FU and hmUdR in a more rigorous fashion, we calculated combination indexes for each cell line. The combination index method was developed to evaluate drug interaction, based on the multiple drug-effect equation of Chou-Talalay (22). These indexes can be interpreted as follows: very strong synergism for <0.1; strong synergism for 0.1-0.3; synergism for 0.3-0.7; moderate to slight synergism for 0.7-0.9; nearly additive for 0.9-1.1 (13). As shown in Table 1, the combination indexes of the tumor cell lines were 0.11 or less at low concentrations of 5-FU. In contrast, the HUVECs had a combination index of 0.34, and the combination indexes for the WI-38, SID507 and SID509 cell lines were not obtained because their growth inhibition did not reach 50%. Taken together, these findings reinforce the notion that the combination treatment of 5-FU and hmUdR selectively impairs the viability of cancer cells compared with normal cells.

Discussion

5-FU has been a mainstay of chemotherapy for colon cancer and other malignancies. Currently, it is frequently used in combination therapies with other genotoxic agents, such as oxaliplatin and irinotecan (2). In this study, we report the novel and unexpected observation that the deoxyuridine analogs, hmUdR, hUdR and foUdR, synergistically enhance the sensitivity of a variety of cell lines derived from solid tumors but not cell lines from normal tissues to 5-FU. Notably, this synergy was independent of p53 status and occurred in mismatch repair-defective HCT 116 cells (23) that also harbor a mutation in the thymidylate synthase gene that may confer some resistance to 5-FU (24, 25).

5-FU exerts pleiotropic effects on nucleic acid metabolism, disrupting RNA metabolism, nucleotide biosynthesis and DNA replication and repair. While our results do not exclude the possibility that the combination of 5-FU and the deoxyuridine analogs synergistically inhibit RNA metabolism, the dramatic increase in DNA single strand breaks indicates that the combination of 5-FU with one of the active deoxyuridine analogs is synergistically impacting the integrity of genomic DNA. In support of this, we observed that much lower concentrations of 5-FUdR (5 nM versus 500 nM 5-FU), which results in significantly more 5-FU incorporation into DNA compared with 5-FU (26), were required to synergistically inhibit cell proliferation and viability with hmUdR.

Furthermore, while cells treated with the combination of 5-FU and one of the deoxyuridine analogs accumulate a large number of DNA single strand breaks and arrest in S phase, the S phase arrest was alleviated by the addition of PARP inhibitors. Thus, it is unlikely that alterations in nucleotide pools resulting from inhibition of thymidylate synthase or other enzymes involved in nucleotide biosynthesis are responsible for the inhibition of DNA replicative synthesis by the combination of 5-FU and one of the active deoxyuridine analogs. Instead, it is more likely that dNTP and ATP levels are reduced indirectly as a result of NAD depletion resulting from PARP1 activation by the single strand breaks.

Although PARP1 participates in many different aspects of DNA metabolism, it is a key player in the efficient repair of DNA single strand breaks, generating the signal, poly(ADP-ribose) that recruits single strand break repair proteins to the damage site (15). Recently PARP inhibitors have been developed as cancer therapeutics because of their ability to cause replication-dependent DNA double strand breaks. These lesions cannot be repaired in cancers, such as hereditary forms of breast and ovarian cancer, that are defective in recombinational repair, resulting in cell death by apoptosis (27). Conversely, DNA damaging agents such as DNA alkylating agents that generate large number of single strand breaks activate PARP1. This in turn induces a necrotic cell death as a consequence of NAD depletion that has been termed programmed necrosis (12, 21). Our results indicate that the combination of 5-FU and hmUdR induces programmed necrosis since cell death is dependent on PARP activity, occurs in actively proliferating cells and is triggered by DNA damage. Interestingly, if PARP1-dependent necrosis is suppressed with a PARP inhibitor, the cells accumulate at $G_2$/M as a result of activation of an ATR/ATM-dependent checkpoint and then die by an as yet undefined mechanism.

It is likely that the single strand breaks observed in cells treated with 5-FU and hmUdR result from their misincorporation during DNA replication followed by their removal by base excision repair (28-30). Interestingly, hmUdR increases the incorporation of Ara-C, another pyrimidine analog inhibitor of DNA replication and nucleotide metabolism that is used primarily in the treatment of acute myeloid and acute lymphocytic anemia, to inhibit cell growth (10). In contrast, hmUdR did not increase the incorporation of 5-FU nor vice versa, indicating that a different mechanism underlies the synergistic activity of 5-FU and hmUdR. It has been reported that the toxicity of 5-FU correlates with thymine DNA glycosylase activity (30) whereas deficiency in 5-hydroxymethyluracil-DNA-glycosylase (SMUG1) activity confers resistance to hmUdR (31). 5-FUrthermore, SMUG1 is also the major enzyme responsible for the removal of foU and hU (32), two of the deoxyuridine analogs that exhibited synergistic activity with 5-FU. 5-FUrther studies are needed to determine whether the substrate specificity and activity of SMUG1 with the deoxyuridine derivatives correlates with the ability of the deoxyuridine derivatives to act synergistically with 5-FU. Since there was no increase in incorporation of modified nucleotides when cells were co-incubated with 5-FU and hmUdR, it seems unlikely that the single strand breaks are generated simply as a consequence of exceeding the capacity of the steps following base removal in the base excision repair pathway. However, it is conceivable that, while alterations in nucleotide pools caused by 5-FU and, possibly hmUdR, do not significantly impact replicative DNA synthesis, they may inhibit repair DNA synthesis. For example, the Km of Pol β for dNTP is significantly higher that of Pol δ (33, 34). In this scenario, we suggest that the synergistic increase in single strand breaks generated in cells co-incubated with 5-FU and hmUdR is caused by incomplete repair of misincorporated 5-FU and hmUdR due to inhibition of repair synthesis.

In summary, we have found that several deoxyuridine analogs synergistically enhance the cytotoxicity of both 5-FU and 5-FUdR, in cancer but not normal cells. Since both these drugs have been used extensively in the treatment of solid tumors, our results provide a rationale for the development of novel 5-FU-based therapies that may more effective both in terms of treating the tumors and in reducing toxicity to normal tissues and cells.

TABLE 1

Growth Inhibition and Combination Index of FU and hmUdR

| | Growth Inhibition (%) with 1 µM FU + 10 µM hmUdR | Combination Index for GI50 |
|---|---|---|
| Cancer cells | | |
| HT-29 (colon) | 89 ± 0.6 | 0.019 |
| HCT 116 (colon) | 92 ± 3.0 | 0.11 |
| PANC-1 (pancreas) | 59 ± 5.5 | <0.054 [2] |
| EKVX (lung) | 77 ± 0.2 [1] | <0.027 [2] |
| Normal cells | | |
| WI-38 (lung) | 11 ± 5.8 | ND [3] |
| HUVEC (umbilical vein) | 44 ± 5.2 | 0.34 |
| SID507 (colon) | 37 ± 4.5 [4] | ND |
| SID509 (colon) | −30 ± 5.4 [4] | ND |

[1] Treatment with 0.5 µM FU + 10 µM hmUdR.
[2] GI50 of hmUdR was not determined but assumed as more than 300 µM.
[3] Not determined.
[4] Treatment with 3 µM FU + 10 µM hmUdR for 7 days.

References for Background of the Invention and Example 1

1. Grem J L. 5-Fluorouracil: forty-plus and still ticking. A review of its preclinical and clinical development. Investigational New Drugs 2000; 18:299-313.
2. O'Connor O A. Pharmacological Modulation of Fluoropyrimidines: Building on the Lessons of the Past. In: Schwartz G K, editor. Combination Cancer Therapy: Modulators and Potentiators. Totowa, N.J.: Humana Press; 2005 p.133-74.
3. Yoshida K, Yamaguchi K, Osada S, Kawaguchi Y, Takahashi T, Sakashita F, et al. Challenge for a better combination with basic evidence. Int J Clin Oncol 2008; 13:212-9.
4. Lewis H L, Muhleman D R, Ward J F. Serologic assay of DNA base damage. I. 5-Hydroxymethyldeoxyuridine, a radiation product of thymidine. Radiation Research 1978; 75:305-16.
5. Teebor G W, Frenkel K, Goldstein M S. Ionizing radiation and tritium transmutation both cause formation of 5-hydroxymethyl-2'-deoxyuridine in cellular DNA. Proc Natl Acad Sci USA 1984; 81:318-21.
6. Kahilainen L I, Bergstrom D E, Vilpo J A. 5-Hydroxymethyl-2'-deoxyuridine. Cytotoxicity and DNA incorporation studied by using a novel [2-$^{14}$C]-derivative with normal and leukemic human hematopoietic cells. Acta Chemi Scand 1985; 39:477-84.
7. Meldrum J B, Gupta V S, Lowes N R, Paterson A R. Toxicologic and antitumor studies on 5-hydroxymethyldeoxyuridine. Toxicol Appl Pharmacol 1985; 79:423-35.
8. Kahilainen L, Bergstrom D, Kangas L, Vilpo J A. In vitro and in vivo studies of a promising antileukemic thymidine analogue, 5-hydroxymethyl-2' deoxyuridine. Biochem Pharmacol 1986; 35:4211-5.
9. Vilpo J A, Suvanto E, Kangas L. Antileukemic activity against L1210 leukemia, pharmacokinetics and hematological side effects of 5-hydroxymethyl-2'-deoxyuridine. Leuk Res 1987; 11:877-80.
10. Vilpo J A, Vilpo L M. Metabolism, incorporation into DNA, and interactions with 1-beta-D-arabino5-FUranosylcytosine of 5-hydroxymethyl-2'-deoxyuridine in human promyelocytic leukemia cells (HL-60). Cancer Res 1988; 48:3117-22.

11. Yoshida M, Makino K, Morita H, Terato H, Ohyama Y, Ide H. Substrate and mispairing properties of 5-formyl-2'-deoxyuridine 5'-triphosphate assessed by in vitro DNA polymerase reactions. Nucleic Acids Res 1997; 25:1570-7.

12. Zong W X, Ditsworth D, Bauer D E, Wang Z Q, Thompson C B. Alkylating DNA damage stimulates a regulated form of necrotic cell death. Genes Dev 2004; 18:1272-82.

13. Reynolds C P, Maurer B J. Evaluating response to antineoplastic drug combinations in tissue culture models. Methods Mol Med 2005; 110:173-83.

14. Rogstad D K, Darwanto A, Herring J L, Rogstad K N, Burdzy A, Hadley S R, et al. Measurement of the incorporation and repair of exogenous 5-hydroxymethyl-2'-deoxyuridine in human cells in culture using gas chromatography-negative chemical ionization-mass spectrometry. Chem Res Toxicol 2007; 20:1787-96.

15. Schreiber V, Dantzer F, Ame J C, de Murcia G. Poly(ADP-ribose): novel 5-FUnctions for an old molecule. Nat Rev Mol Cell Biol 2006; 7:517-28.

16. Vaculova A, Hofmanova J, Soucek K, Kozubik A. Different modulation of TRAIL-induced apoptosis by inhibition of pro-survival pathways in TRAIL-sensitive and TRAIL-resistant colon cancer cells. FEBS Lett 2006; 580:6565-9.

17. Caserta T M, Smith A N, Gultice A D, Reedy M A, Brown T L. Q-VD-OPh, a broad spectrum caspase inhibitor with potent antiapoptotic properties. Apoptosis 2003; 8:345-52.

18. Bjorkoy G, Lamark T, Brech A, Outzen H, Perander M, Overvatn A, et al. p62/SQSTM1 forms protein aggregates degraded by autophagy and has a protective effect on huntingtin-induced cell death. J. Cell Biol 2005; 171:603-14.

19. Kabeya Y, Mizushima N, Ueno T, Yamamoto A, Kirisako T, Noda T, et al. LC3, a mammalian homologue of yeast Apg8p, is localized in autophagosome membranes after processing. EMBO J 2000; 19:5720-8.

20. Degterev A, Huang Z, Boyce M, Li Y, Jagtap P, Mizushima N, et al. Chemical inhibitor of nonapoptotic cell death with therapeutic potential for ischemic brain injury. Nat Chem Biol 2005; 1:112-9.

21. Edinger A L, Thompson C B. Death by design: apoptosis, necrosis and autophagy. Curr Opin Cell Biol 2004; 16:663-9.

22. Chou T C, Talalay P. Quantitative analysis of dose-effect relationships: the combined effects of multiple drugs or enzyme inhibitors. Adv Enzyme Regul 1984; 22:27-55.

23. Papadopoulos N, Nicolaides N C, Wei Y F, Ruben S M, Carter K C, Rosen C A, et al. Mutation of a mutL homolog in hereditary colon cancer. Science 1994; 263:1625-9.

24. Berger S H, Barbour K W, Berger F G. A naturally occurring variation in thymidylate synthase structure is associated with a reduced response to 5-fluoro-2'-deoxyuridine in a human colon tumor cell line. Mol Pharmacol 1988; 34:480-4.

25. Berger S H, Berger F G. Thymidylate synthase as a determinant of 5-fluoro-2'-deoxyuridine response in human colonic tumor cell lines. Mol Pharmacol 1988; 34:474-9.

26. Pettersen H S, Visnes T, Vågbø C B, Svaasand E K, Doseth B, Slupphaug G, et al. UNG-initiated base excision repair is the major repair route for 5-fluorouracil in DNA, but 5-fluorouracil cytotoxicity depends mainly on RNA incorporation. Nucleic Acids Res 2011; 39:8430-44.

27. Peralta-Leal A, Rodriguez M I, Oliver F J. Poly(ADP-ribose)polymerase-1 (PARP-1) in carcinogenesis: potential role of PARP inhibitors in cancer treatment. Clin Transl Oncol 2008; 10:318-23.

28. Boorstein R J, Cummings A Jr, Marenstein D R, Chan M K, Ma Y, Neubert T A, et al. Definitive identification of mammalian 5-hydroxymethyluracil DNA N-glycosylase activity as SMUG1. J Biol Chem 2001; 276: 41991-7.

29. An Q, Robins P, Lindahl T, Barnes D E. 5-Fluorouracil incorporated into DNA is excised by the Smug1 DNA glycosylase to reduce drug cytotoxicity. Cancer Res 2007; 67:940-5.

30. Kunz C, Focke F, Saito Y, Schuermann D, Lettieri T, Selfridge J, et al. Base excision by thymine DNA glycosylase mediates DNA-directed cytotoxicity of 5-fluorouracil. PLoS Biol 2009; 10.1371/journal.pbio.1000091.

31. Boorstein R J, Chiu L N, Teebor G W. A mammalian cell line deficient in activity of the DNA repair enzyme 5-hydroxymethyluracil-DNA glycosylase is resistant to the toxic effects of the thymidine analog 5-hydroxymethyl-2'-deoxyuridine. Mol Cell Biol 1992; 12:5536-40.

32. Masaoka A, Matsubara M, Hasegawa R, Tanaka T, Kurisu S, Terato H, et al. Mammalian 5-formyluracil-DNA glycosylase. 2. Role of SMUG1 uracil-DNA glycosylase in repair of 5-formyluracil and other oxidized and deaminated base lesions. Biochemistry 2003; 42:5003-12.

33. Nemec A A, Donigan K A, Murphy D L, Jaeger J, Sweasy J B. Colon cancer-associated DNA polymerase β variant induces genomic instability and cellular transformation. J Biol Chem 2012; 287:23840-9.

34. Einolf H J, Guengerich F P. Kinetic analysis of nucleotide incorporation by mammalian DNA polymerase delta. J Biol Chem 2000; 275:16316-22.

Example 2

Synergistic Combinations of (1) 5-formyl-2'-deoxyuridine (fdU) or 5-hydroxy-2'-deoxyuridine (hUdR) and (2) 5-fluorouracil (5-FU) or 5-fluoro-2'-deoxyuridine (FdU).

In Example 2, all references to Figures relate to FIGS. 10-13. A reference to "FIG. 10-A" means FIG. 10, panel A.

Here we demonstrate that synergistic combinations of (1) 5-formyl-2'-deoxyuridine (fdU) or 5-hydroxy-2'-deoxyuridine (hUdR) and (2) 5-fluorouracil (5-FU) or the 5-FU prodrug 5-fluoro-2'-deoxyuridine (FdU) synergistically induce programmed necrosis in HT-29 cancer cells. As was determined in the experiment of Example 1 involving co-administration of 5-FU and hmUdR, HT-29 cell death was found to occur in actively proliferating cells and was triggered by DNA damage. Significantly, cytotoxic dosages of 5-formyl-2'-deoxyuridine (fdU) were found to be lower than cytotoxic hmUdR dosages used in the co-administration of 5-FU and hmUdR in the experiment of Example 1.

Figure 10:
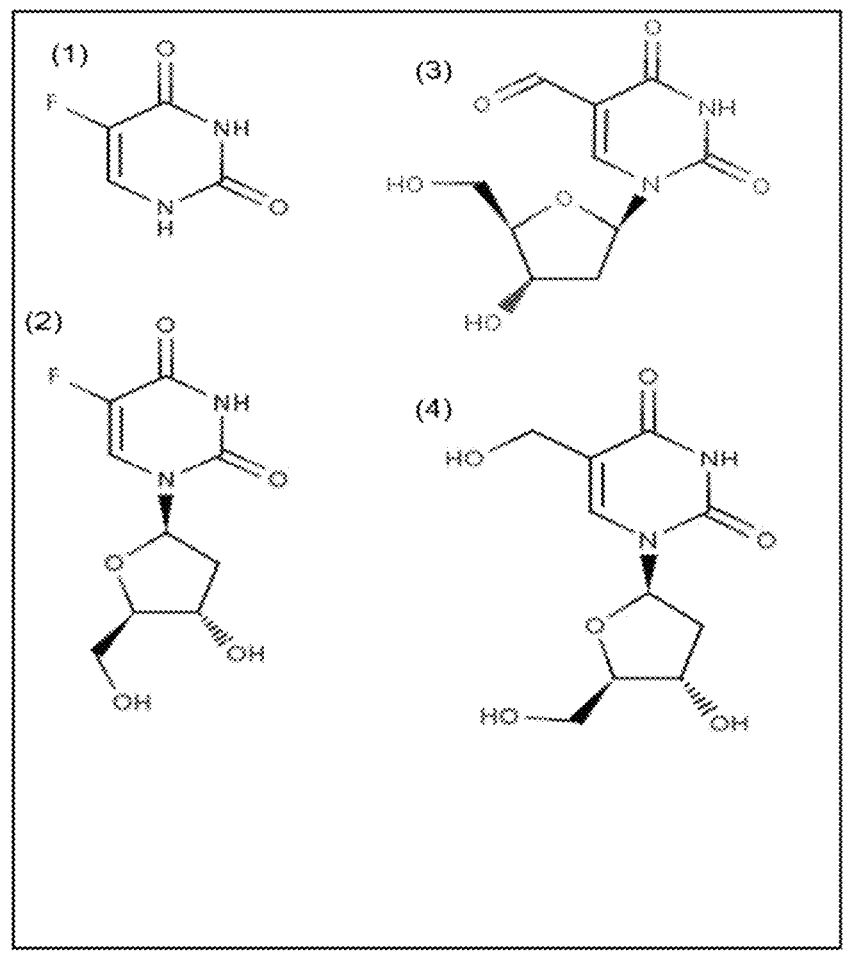
FIG. 10. Chemical structures of 5-fluorouracil (5-FU) (1), 5-fluoro-2'-deoxyuridine (FdU) (2), 5-formyl-2'-deoxyuridine (fdU) (3) and 5-hydroxymethyl-2'-deoxyuridine (HmdU) (4).

FIG. 10 depicts the chemical structures of 5-fluorouracil (5-FU) (1), 5-fluoro-2'-deoxyuridine (FdU) (2), 5-formyl-2'-deoxyuridine (fdU) (3) and 5-hydroxymethyl-2'-deoxyuridine (HmdU) (4).

Figure 11:
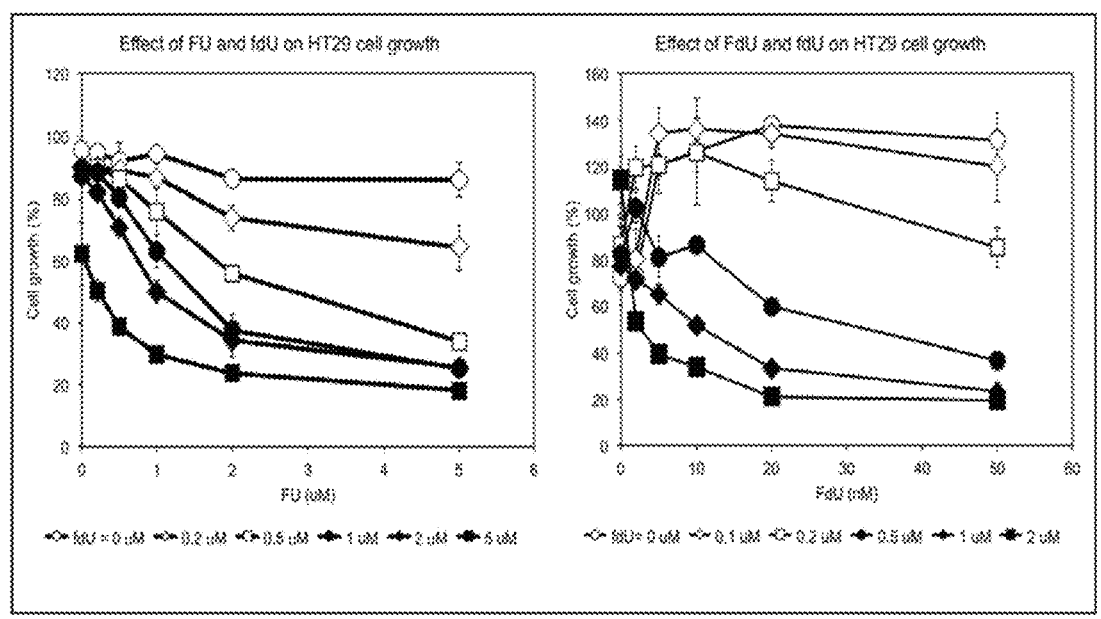
FIG. 11. Cell growth assays of HT-29 cells treated with 5-FU and fdU (A) or FdU and fdU (B).

The results of cell growth assays in which human CRC HT-29 cells were treated with 5-FU and fdU (A) or FdU and fdU (B) are shown in FIG. 11. As seen in FIG. 11, increasing concentrations of fdU at constant 5-FU and FdU concentrations substantially reduced HT-29 cell growth. Increasing the concentration of 5-FU or FdU in the absence of fdU had a minimal effect on HT-29 cell growth. A comparison of relative growth inhibitory dosages depicted in FIG. 11 and FIG. 6, panel A (Example 1) shows that for a given 5-FU dosage, the dosages of fdU required for a combination of 5-FU-fdU to achieve a particular level of cell growth inhibition are lower than the dosage of hmUdR required for a combination of 5-FU-hmUdR to achieve that same level of cell growth inhibition.

Figure 12:
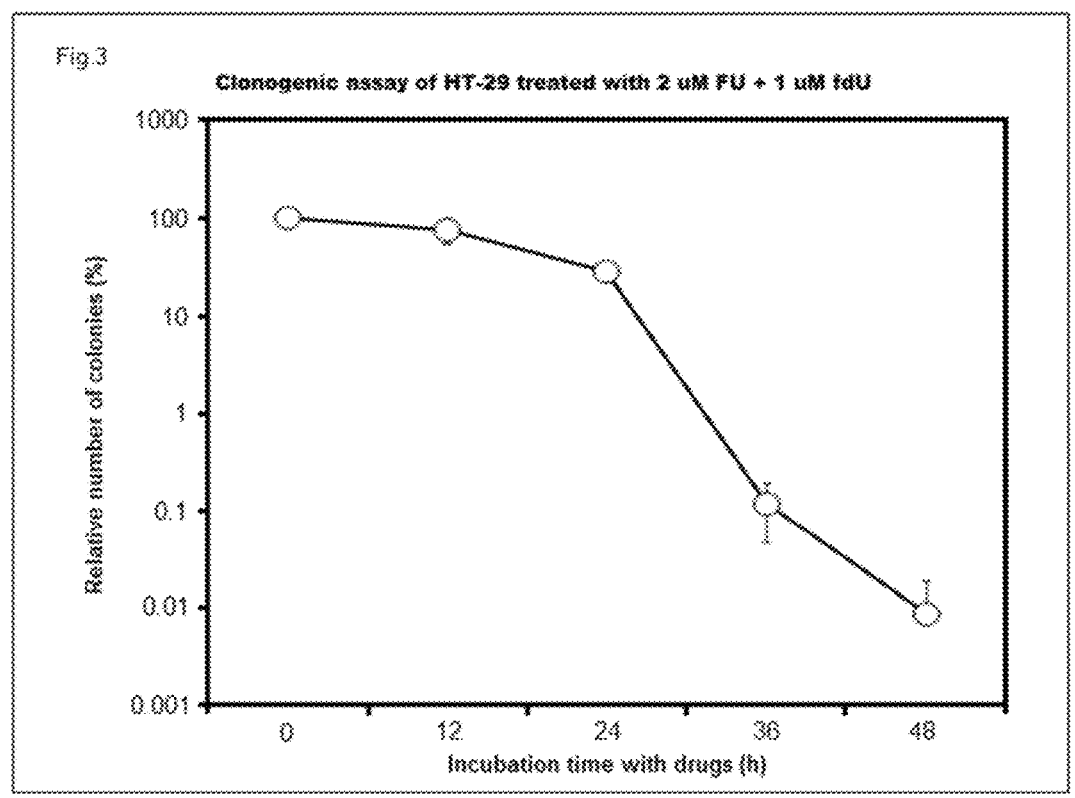
FIG. 12. Clonogenic assay of HT-29 treated with 2 μM 5-FU and 1 μM fdU.
Figure 13:
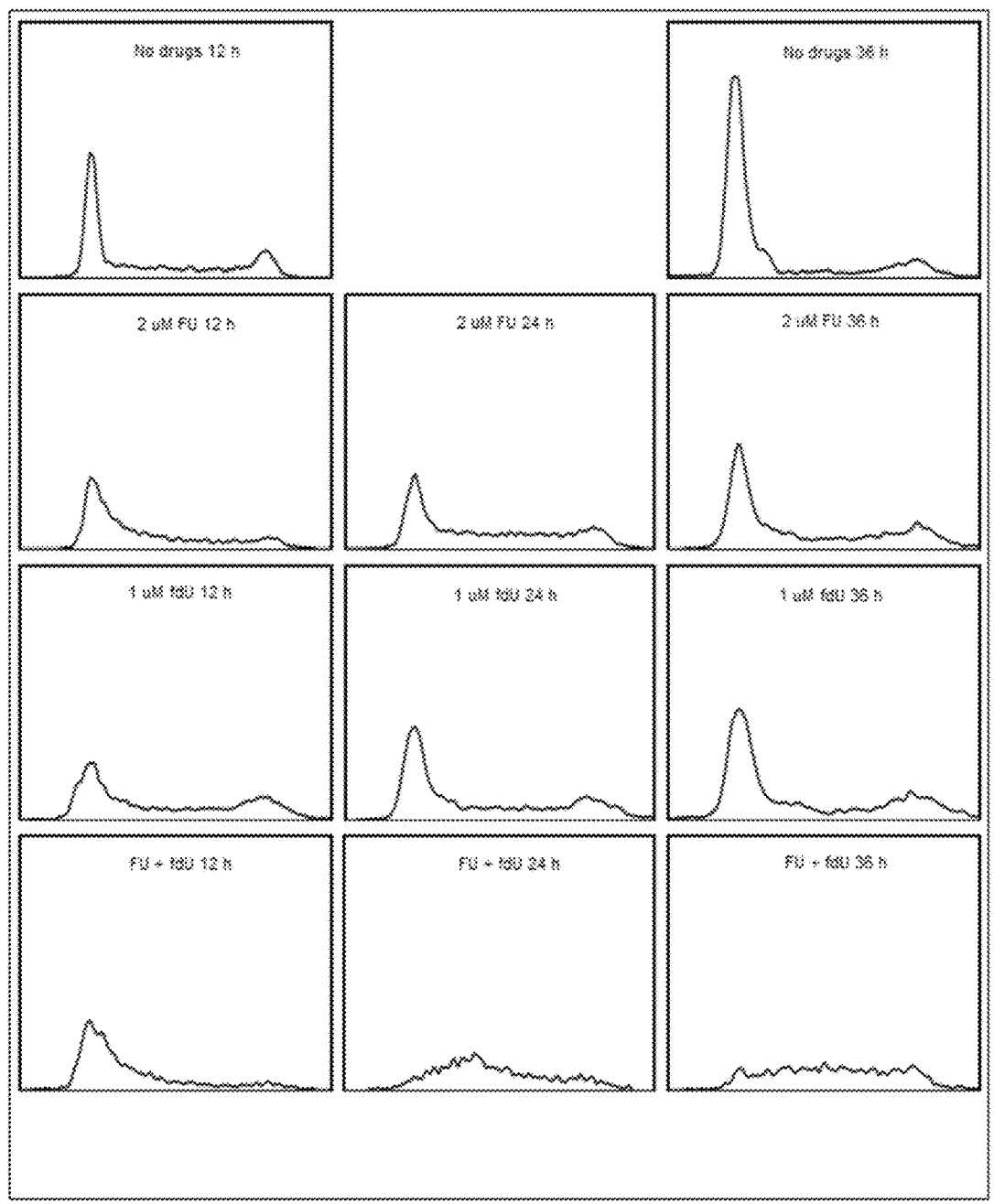
FIG. 13. Cell cycle analysis of HT-29 cells treated with indicated drugs for 0-36 hours.

For clonogenic assays, HT-29 cells were plated in six-well plates and treated the day after with 2 µM 5-FU and 1 µM fdU for 0-48 hours. After removal of drug-containing medium, cells were trypsinized and plated at low density with appropriate dilutions in 35-mm plates. Cells were then cultivated for ten days and colonies were stained with methylene blue. Clones in a given area were counted for each condition. All assays were done in triplicate. As shown in FIG. 12, an almost thousand-fold drop in the relative number of colonies (%) was observed between about twenty-four to about thirty-six hours after initiation of cell treatment.

Cell cycle analyses of HT-29 cells by flow cytometry were undertaken. A time course of cell cycle distribution was determined for synchronized cells that were (1) untreated (2) treated with 2 µM 5-FU (3) treated with 1 µM fdU, and (4) treated with a combination of 2 µM 5-FU and 1 µM fdU. HT-29 cells were synchronized at the $G_1$/S boundary by sequential pretreatment with nocodazole and aphidicolin as described in the Materials and Methods of Example 1. The time at which aphidicolin was removed is designated 0 h. When indicated, 5-FU and/or fdU were added through aphidicolin treatment and subsequent incubation.

Similar to the cell cycle analysis for HT-29 treated with 5-FU and hmUdR in the experiment of Example 1 (see FIG. 2), HT-29 treated with 5-FU and fdU accumulated in S phase. Following removal of aphidicolin and incubation for 12 h, 33% of untreated cells and 42% of treated cells were in S phase. By 36 h, the untreated cell population exhibited a normal cell cycle distribution with a major $G_1$ population. In contrast, the majority of treated cells remained in S phase for at least 36 h after the removal of aphidicolin. See FIG. 13.

What is claimed is:

1. A method of treating a neoplasm, the method comprising administering to a subject in need thereof a therapeutically effective amount of:
   (a) 5-formyl-2'-deoxyuridine (fdU) or a 5-formyl-2'-deoxyuridine (fdU) derivative, optionally in combination with 5-hydroxy-2'-deoxyuridine (hUdR); and
   (b) at least one composition selected from the group consisting of 5-fluorouracil (5-FU), a 5-fluorouracil (5-FU) prodrug and a 5-FU metabolite.

2. The method of claim 1, wherein:
   (a) the 5-fluorouracil (5-FU) prodrug is selected from the group consisting of 5-fluoro-2'-deoxyuridine (FdU), 5'-deoxy-5-fluoro-N-[(pentyloxy) carbonyl]-cytidine (capecitabine), 13F-1 (a 5-fluorouracil prodrug containing an Asn-Gly-Arg ($NO_2$) $COOCH_3$ tripeptide), 1-(2-tetrahydrofuryl)-5-fluorouracil, 3, 5-dioctanoyl 5-fluoro-2-deoxyuridine, UFT (ftorafur (FTO) and uracil), S-1 (ftorafur (FTO) and 5-chloro-2,4-dihydroxypyridine plus potassium oxonate), 5-FA-PAE (5-fluorouracil-1 acetic acid (5-FA) coupled with PEG derivatives by an ester bond), 5-FU-lipid conjugates, hyaluronan-5-fluorouracil conjugate (HA-5-Fu), cholesteryl-hexahydrophthaloyl-5-fluorouracil (CHHP-5-FU)), tegafur (tetrahydrofuranyl-5-fluorouracil) and uracil (1:4); and
   (b) the 5-FU metabolite is fluorodeoxyuridine monophosphate (FdUMP), fluorodeoxyuridine triphophate (FdUTP) or fluorouridine triphosphate (FUTP).

3. The method of claim 1, wherein the subject is co-administered 5-formyl-2'-deoxyuridine (fdU) and either 5-FU or 5-fluoro-2'-deoxyuridine (FdU).

4. The method of claim 1, wherein 5-formyl-2'-deoxyuridine (fdU) is in the form of a mixture of α-anomers and β-anomers.

5. The method of claim 1, wherein 5-formyl-2'-deoxyuridine (fdU) is in the form of a substantially purified α-anomer.

6. The method of claim 1, wherein 5-formyl-2'-deoxyuridine (fdU) is in the form of a substantially purified β-anomer.

7. The method of claim 1, wherein the sugar group of 5-formyl-2'-deoxyuridine (fdU), 5-formyl-2'-deoxyuridine (fdU) derivative and 5-hydroxy-T-deoxyuridine (hUdR) is halogenated.

8. The method of claim 7, wherein the sugar group of 5-formyl-2'-deoxyuridine (fdU), 5-formyl-2'-deoxyuridine (fdU) derivative and 5-hydroxy-2'-deoxyuridine (hUdR) is halogenated with either chlorine or fluorine.

9. The method of claim 1, wherein 5-formyl-2'-deoxyuridine (fdU) is protected.

10. The method of claim 9, wherein 5-formyl-2'-deoxyuridine (fdU) is protected by converting the 5-formyl-2'-deoxyuridine (fdU) carbonyl group to either an acetal or hydrazide group ex vivo, said acetal and hydrazine group converting in vivo to a carbonyl group.

11. The method of claim 1, wherein the subject is administered concomitantly:
    (a) 5-formyl-2'-deoxyuridine (fdU), optionally in combination with 5-hydroxy-T-deoxyuridine (hUdR); and
    (b) 5-fluorouracil (5-FU) and/or 5-fluoro-2'-deoxyuridine (FdU) and/or and pentyl [1-(3,4-dihydroxy-5-methyltetrahydrofuran-2-yl)-5-fluoro-2-oxo-1H-pyrimidin-4-yl] carbamate (capecitabine).

12. The method of claim 1, wherein the subject suffers from a cancer.

13. The method of claim 12, wherein at least one additional anti-cancer agent or anti-cancer therapy is co-administered to the subject.

14. The method of claim 13, wherein the subject is treated by an additional therapy and/or therapeutic agent selected from the group consisting of one or more additional chemotherapeutic agents such as paclitaxel and docetaxel, platinum-based antineoplastics, hormonal therapy, proton therapy, cryosurgery, and/or high intensity focused ultrasound (HIFU).

15. The method of claim 1, wherein one or more PARP inhibitors are co-administered to the subject.

16. The method of claim 1, wherein the subject suffers from a cancer selected from the group consisting of colorectal cancer (CRC), breast cancer, ovarian cancer, glioblastoma multiform (GBM), melanoma, lung cancer and a glioma and is co-administered a therapeutically-effective amount of (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR).

17. The method of claim 16, wherein the subject is treated concomitantly by radiotherapy and is optionally treated with a radiosensitizer prior to or during radiotherapy.

18. The method of claim 1, wherein the subject suffers from a treatment-resistant cancer selected from the group consisting of metastatic colorectal cancer (mCRC), breast cancer in which BRCA1-deficient cells exhibit decreased sensitivity to PARP inhibitors, ovarian cancer which is resistant to platinum-containing anti-neoplastic drugs, hormone and castration-resistant prostate cancer, metastatic melanoma, drug resistant childhood acute lymphoblastic leukemia (ALL) and radiotherapy-resistant glioblastomas, cervical cancer, esophageal cancer (EC), breast cancers and non-small cell lung cancer.

19. The method of claim 1, wherein the subject suffers from colorectal cancer (CRC) or metastatic colorectal cancer (mCRC) and is treated with a therapeutically-effective amount of:
 (a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
 (b) an EGFR-directed treatment.

20. The method of claim 1, wherein the subject suffers from BRCA-associated or refractive breast or ovarian cancer and is co-administered a therapeutically-effective amount of:
 (a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
 (b) one or more additional anti-cancer agents selected from the group consisting of a chemotherapeutic agent, a HER antibody, an antibody directed against a tumor associated antigen, an anti-hormonal compound, a cardioprotectant, a cytokine, an EGFR-targeted drug, an anti-angiogenic agent, a tyrosine kinase inhibitor, a COX inhibitor, a non-steroidal anti-inflammatory drug, a farnesyl transferase inhibitor, an antibody that binds oncofetal protein CA 125, HER2 vaccine, HER targeting therapy, Raf or ras inhibitor, doxorubicin, topotecan, taxane, a dual tyrosine kinase inhibitor, TLK286 and EMD-7200, Rucaparib and a PARP inhibitor.

21. The method of claim 1, wherein the subject suffers from colorectal cancer or mCRC and is co-administered a therapeutically-effective amount of:
 (a) (1) 5-FU, a 5-fluorouracil (FU) prodrug or a 5-FU metabolite and (2) 5-formyl-2'-deoxyuridine (fdU), optionally in combination with 5-hydroxy-2'-deoxyuridine (hUdR); and
 (b) at least one additional anti-cancer agent selected from the group consisting of (1) oxaliplatin and/or irinotecan, (2) an anti-VEGF-A antibody, (3) an anti-epidermal growth factor receptor (anti-EGFR) antibody, (4) an anti-angiogenic multi-kinase inhibitor, (5) an anti-angiogenic compound, (6) leucovorin.

22. The method of claim 1, wherein the subject suffers from one or more cancers selected from the group consisting of breast cancer, ovarian cancer, non-small-cell lung cancer and prostate cancer.

23. The method of claim 1, wherein the subject suffers from one or more cancers selected from the group consisting of relapsed or refractory T-cell prolymphocytic leukemia (T-PLL), chronic lymphocytic leukemia (CLL), locally advanced or metastatic colorectal carcinoma (CRC), persistent or recurrent endometrial carcinoma, locally advanced or metastatic triple negative or highly proliferative estrogen receptor positive (ER+) breast cancer and partially platinum-sensitive epithelial ovarian cancer.

24. A pharmaceutical formulation which is useful in the treatment of a neoplasm, the pharmaceutical formulation comprising a therapeutically-effective amount of:
 (a) one or more active ingredients selected from the group consisting of 5-FU, a 5-fluorouracil (FU) prodrug or a 5-FU metabolite;
 (b) 5-formyl-2'-deoxyuridine (fdU) or a 5-formyl-2'-deoxyuridine (fdU) derivative, optionally in combination with 5-hydroxy-2'-deoxyuridine (hUdR); and
 (c) optionally, a pharmaceutically acceptable excipient.

25. The pharmaceutical formulation of claim 24, wherein the pharmaceutical formulation is useful in the treatment of a cancer and comprises one or more additional anti-cancer agents.

26. The pharmaceutical formulation of claim 25, wherein the pharmaceutical formulation comprises one or more PARP inhibitors.

27. The pharmaceutical formulation of claim 25, wherein the pharmaceutical formulation comprises one or more platinum-based antineoplastic drugs.

28. A method of treating a subject who suffers from a malignant tumor, the method comprising inducing programmed necrosis in cancerous tumor cells by co-administering to the subject:
 (a) 5-formyl-2'-deoxyuridine (fdU) or a 5-formyl-2'-deoxyuridine (fdU) derivative, optionally in combination with 5-hydroxy-2'-deoxyuridine (hUdR); and
 (b) at least one compound selected from the group consisting of 5-fluorouracil (5-FU), a fluorouracil (5-FU) prodrug and a 5-FU metabolite.

29. The method of claim 1, wherein:
 (a) the 5-fluorouracil (5-FU) prodrug is selected from the group consisting of 5-fluoro-2'-deoxyuridine (FdU), 5'-deoxy-5-fluoro-N-[(pentyloxy) carbonyl]-cytidine (Capecitabine), 13F-1 (a 5-fluorouracil prodrug containing an Asn-Gly-Arg ($NO_2$) $COOCH_3$ tripeptide), 1-(2-tetrahydrofuryl)-5-fluorouracil, 3, 5-dioctanoyl 5-fluoro-2-deoxyuridine, UFT (ftorafur (FTO) and uracil), S-1 (ftorafur (FTO) and 5-chloro-2,4-dihydroxypyridine plus potassium oxonate), 5-FA-PAE (5-fluorouracil-1 acetic acid (5-FA) coupled with PEG derivatives via ester bond), 5-FU-lipid conjugates, hyaluronan-5-fluorouracil conjugate (HA-5-Fu), cholesteryl-hexahydrophthaloyl-5-fluorouracil (CHHP-5-FU)), tegafur (tetrahydrofuranyl-5-fluorouracil) and uracil (1:4); and
 (b) the 5-FU metabolite is fluorodeoxyuridine monophosphate (FdUMP), fluorodeoxyuridine triphophate (FdUTP) or fluorouridine triphophate (FUTP).

30. The method of claim 28, wherein 5-formyl-2'-deoxyuridine (fdU) is co-administered to the subject.

31. The method of claim 28, wherein PARP1-dependent necrosis is induced in malignant tumor cells.

32. The method of claim 28, wherein a PARP inhibitor is co-administered to the subject.

33. The method of claim 28, wherein the 5-FU prodrug is 5-fluoro-2'-deoxyuridine (FdU).

34. The method of claim 28, the method further comprising treating the subject with an additional therapy and/or therapeutic agent selected from the group consisting of paclitaxel, docetaxel, a platinum-based antineoplastic, hormonal therapy, proton therapy, cryosurgery, and/or high intensity focused ultrasound (HIFU).

35. The method of claim 28, wherein the tumor is a metastatic colorectal cancer (mCRC) tumor and wherein the subject is co-administered therapeutically-effective amounts of:
  (a) (1) 5-fluoro-2'-deoxyuridine (FdU) and (2) 5-FU or 5-fluoro-2'-deoxyuridine (FdU); and
  (b) at least one additional anti-cancer agent selected from the group consisting of (1) oxaliplatin and/or irinotecan, (2) an anti-VEGF-A antibody, (3) an anti-epidermal growth factor receptor (anti-EGFR) antibody, (4) an anti-angiogenic multi-kinase inhibitor, (5) an anti-angiogenic compound, and (6) leucovorin.

36. The method of claim 28, wherein the subject is co-administered therapeutically-effective amounts of:
  (a) (1) 5-fluoro-2'-deoxyuridine (FdU) and (2) 5-FU or 5-fluoro-2'-deoxyuridine (FdU); and
  (b) one or more additional anti-cancer agents selected from the group consisting of Regorafenib (BAY 73-4506), bevacizumab, cetuximab, oxaliplatin, irinotecan, leucovorin, MK-4827 and CEP-9722.

37. The method according to claim 14 wherein said additional therapeutic agent is at least one agent selected from group consisting of paclitaxel, docetaxel, cisplatin, carboplatin, oxaliplatin, satraplatin, picoplatin, nedaplatin, triplatin, and lipoplatin.

38. The method according to claim 19 wherein said EGFR treatment is the co-administration of cetuximab and panitumumab.

39. The method according to claim 21 wherein said said anti-VEGF-A antibody is bevacizumab, said EGFR antibody is cetuximab or panitumumab, said anti-angiogenic multi-kinase is regorafenib and said anti-angiogenic compound is aflibercept.

40. The method according to claim 34 wherein said platinum based antineoplastic agent is selected from group consising of cisplatin, carboplatin, oxaliplatin, satraplatin, picoplatin, nedaplatin, triplatin, and lipoplatin.

41. The method according to claim 35 wherein said said anti-VEGF-A antibody is bevacizumab, said EGFR antibody is cetuximab or panitumumab, said anti-angiogenic multi-kinase is regorafenib and said anti-angiogenic compound is aflibercept.

* * * * *